US009243046B2

(12) United States Patent
Leung et al.

(10) Patent No.: US 9,243,046 B2
(45) Date of Patent: Jan. 26, 2016

(54) VARIANTS OF HUMAN GDNF

(75) Inventors: Donmienne Doen Mun Leung, San Diego, CA (US); Jirong Lu, Carmel, IN (US); Kalpana Mahesh Merchant, Zionsville, IN (US); Mahmoud Ghanem, Indianapolis, IN (US); Linda Maureen O'Bryan, Indianapolis, IN (US); Rosamund Carol Smith, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 127 days.

(21) Appl. No.: 14/000,704

(22) PCT Filed: Apr. 3, 2012

(86) PCT No.: PCT/US2012/031927
§ 371 (c)(1),
(2), (4) Date: Aug. 21, 2013

(87) PCT Pub. No.: WO2012/141936
PCT Pub. Date: Oct. 18, 2012

(65) Prior Publication Data
US 2013/0324474 A1    Dec. 5, 2013

Related U.S. Application Data

(60) Provisional application No. 61/474,024, filed on Apr. 11, 2011.

(51) Int. Cl.
*A61K 38/18* (2006.01)
*C07K 14/475* (2006.01)
*C07K 14/47* (2006.01)
*A61K 38/00* (2006.01)

(52) U.S. Cl.
CPC .............. *C07K 14/47* (2013.01); *A61K 38/185* (2013.01); *C07K 14/475* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,042,579 A | 3/2000 | Elsberry et al. | |
| 6,362,319 B1 | 3/2002 | Lin et al. | |
| 7,226,758 B1 | 6/2007 | Lin et al. | |
| 2004/0127419 A1 | 7/2004 | Hu | |
| 2005/0137134 A1 | 6/2005 | Gill et al. | |
| 2011/0245798 A1 | 10/2011 | Gill et al. | |

FOREIGN PATENT DOCUMENTS

| | | | |
|---|---|---|---|
| CN | 101775072 A | 7/2010 | |
| EP | 1014881 B1 | 11/2004 | |
| WO | 9306116 A1 | 4/1993 | |
| WO | 97/11964 | 4/1997 | |
| WO | 9953091 A2 | 10/1999 | |
| WO | 2009053536 A2 | 4/2009 | |

OTHER PUBLICATIONS

Piltonen, M., et al., "Heparin-Binding Determinants of GDNF Reduce Its Tissue Distribution but Are Beneficial for the Protection of Nigral Dopaminergic Neurons," Experimental Neurology, 219, 499-506 (2009).
Lin, L.H., et al., "GDNF: A Glial Cell Line-Derived Neurotrophic Factor for Midbrain Dopaminergic Neurons," Science, 260, 1130-1132 (1993).
Hui, J., et al., "Identification of Asp95 as the Site of Succinimide Formation in Recombinant Human Glial Cell Line-Derived Neurotrophic Factor," Archives of Biochemistry and Biophysics, vol. 358, No. 2, Oct. 15, pp. 377-384 (1998).
Lang, A.E., et al., "Randomized Controlled Trial of Intraputamenal Glial Cell Line-Derived Neurotrophic Factor Infusion in Parkinson Disease," Annals of Neurology, vol. 59, No. 3, pp. 459-466 (2006).
Gill, S.S., et al., "Intraparenchymal Putaminal Administration of Glial-Derived Neurotrophic Factor in the Treatment of Advanced Parkinson's Disease," Neurology 58 Apr. 17, 2002 (Supplement 3).
Gash et al., "Functional recovery in parkinsonian monkeys treated with GDNF" Nature, vol. 380 (1996) pp. 252-255.
Gill et al., "Direct brain infusion of glial cell line-derived neurotrophic factor in Parkinson disease" Nature Medicine (2003) pp. 1-7.
Lang et al., "Randomized Controlled Trial of Intraputamenal Glial Cell Line-Derived Neurotrophic Factor Infusion in Parkinson Disease" Annals of Neurology, vol. 59, No. 3 (2006) pp. 459-466.
Love et al., "Glial cell line-derived neurotrophic factor induces neuronal sprouting in human brain" Nature Medicine, vol. 11, No. 7 (2005) pp. 703-704.
Vastag, "Crossing the Barrier" Nature, vol. 466 (2010) pp. 916-918.
Slevin et al., "Improvement of bilateral motor functions in patients with Parkinson disease through the unilateral intraputaminal infusion of glial cell line-derived neurotrophic factor" J Neurosurg, vol. 102 (2005) pp. 216-222.
Tomac et al., "Protection and repair of the nigrostriatal dopaminergic system by GDNF in vivo" Nature, vol. 373 (1995) pp. 335-339.
Rickard et al., "The binding of human glial cell line-derived neurotrophic factor to heparin and heparan sulfate: importance of 2-O-sulfate groups and effect on its interaction with its receptor, GFRα1" Glycobiology, vol. 13, No. 6 (2003) pp. 419-426.
International Search Report, PCT/US2012/031927, Eli Lilly and Company.
Written Opinion of the International Searching Authority, PCT/US2012/031927, Eli Lilly and Company.
Eketjall et al., "Distinct structural elements in GDNF mediate binding to GFRα1 and activation of the GFRα1-c-Ret receptor complex", The EMBO Journal, vol. 18, No. 21, pp. 5901-5910, 1999.
Piccinini et al., "Glial cell line-derived neurotrophic factor: Characterization of mammalian posttranslational modifications", Annals of Medicine, vol. 45, pp. 66-73, 2013.

(Continued)

*Primary Examiner* — Robert C Hayes
(74) *Attorney, Agent, or Firm* — Kyle W. Grimshaw

(57) ABSTRACT

The present invention relates to novel variants of human glial cell-derived neurotrophic factor (GDNF) and methods for their use.

2 Claims, No Drawings

(56) References Cited

OTHER PUBLICATIONS

Schellekens, "Relationship between biopharmaceutical immunogenicity of epoetin alfa and pure red cell aplasia", Current Medical Research and Opinion, vol. 19, No. 5, pp. 433-434, 2003.

Tatarewicz et al., "Development of a Maturing T-Cell-Mediated Immune Response in Patients with Idiopathic Parkinson's Disease Receiving r-metHuGDNF Via Continuous Intraputaminal Infusion", J Clin Immunol, DOI 10.1007/s10875-007-9117-8, 2007.

Schellekens, "Factors influencing the immunogenicity of therapeutic proteins", Nephrol Dial Transplant, vol. 20, [Suppl 6]: vi3-vi9 doi:10.1093/ndt/gfh1092, 2005.

VARIANTS OF HUMAN GDNF

This application is a U.S. national stage application under 35 U.S.C. §371 of PCT/US2012/031927, filed Apr. 3, 2012, which claims the benefit under 35 U.S.C. §119(e) of U.S. Provisional Application Ser. No. 61/474,024, filed Apr. 11, 2011.

The present invention is in the field of medicine, particularly in the field of therapeutic proteins. Specifically, the present invention relates to novel variants of human glial cell-derived neurotrophic factor (GDNF). The novel variants of GDNF may be useful for the treatment of Parkinson's disease.

GDNF is a well known neurotrophic factor that is reported to provide trophic support to dopaminergic neurons in vitro and in vivo. Further, it has been reported that GDNF provides functional improvements and has neuroprotective actions in rodent and primate models of Parkinson's disease. Wild type GDNF protein from *E. coli* has been administered centrally to patients suffering from Parkinson's disease with mixed results. In two small open labeled studies, the wild type GDNF was reported to produce long-lasting improvement in motor function. However, in a randomized, placebo-controlled, Phase IIa trial of 34 patients, intra-putamenal delivery of GDNF showed no symptomatic improvement at 6 months. An increase in biomarker signal was only evident in the immediate tissue surrounding the infusion site. One recent report states that GDNF may be a promising molecule to rescue dying nerves; however, delivering the molecule to the correct area of the brain remains a daunting challenge. *Nature*, Vol 466:19 Aug. 2010.

Truncated GDNF proteins are reported in WO97/11964 (PCT/US96/14915); however, there continues to be a need for new GDNF variants with desired pharmacological properties, stability and bio-distribution properties. There is a need for a variant form of GDNF that is stable in the delivery device, and facilitates desired brain bio-distribution, while demonstrating desired potency and acceptable immunogenicity properties. GDNF variants offering one or more of these desirable properties may be a new pharmaceutically useful medicinal therapy, particularly for use in the treatment of Parkinson's disease.

The present invention provides a novel truncated GDNF variant of mature human GDNF domain lacking the first 31 amino acids at the N-terminus ("Δ31-N-terminus truncated GDNF"), with certain amino acid substitutions introduced to provide stable, suitably potent, GDNF variants offering desirable bio-distribution properties and a pharmaceutically acceptable immunogenicity profile. The present invention provides certain variants of human GDNF that impart one or more advantages over mature human wild-type GDNF including variants that have improved pharmaceutical stability, as well as improved bio-distribution, reduced heparin binding, reduced deamidation, reduced susceptibility to succinimide formation, and reduced immunogenicity potential compared to human wild-type GDNF. Certain new GDNF variants may be a useful new treatment option for Parkinson's disease patients.

The present invention provides human GDNF variant comprising SEQ ID NO: 23 RGQRGKQRGCVLTAIHLNVT-DLGLGYETKEELIFRYCSGSCDAAETTYDKILXaa$_{84}$ NLSXaa$_{88}$NXaa$_{90}$RLVSEKVGQACCRPIAFDDDLSFLDD NLVYHILRXaa$_{125}$HSAKXaa$_{130}$CGCI (SEQ ID NO: 23), wherein:

i) Xaa$_{84}$ is K or A;
ii) Xaa$_{88}$ is R or K;
iii) Xaa$_{90}$ is R or K;
iv) Xaa$_{125}$ is K or E; and
v) Xaa$_{130}$ is R or E.

The invention further provides a human GDNF variant wherein said variant is selected from the group consisting of (SEQ ID NO: 9)
RGQRGKQRGCVLTAIHLNVTDLGLGYETKEELIFRYCSGSCDAAETTYD

KILKNLSRNRRLVSEKVGQACCRPIAFDDDLSFLDDNLVYHILRKHSAK

RCGCI, (SEQ ID NO: 12)
RGQRGKQRGCVLTAIHLNVTDLGLGYETKEELIFRYCSGSCDAAETTYD

KILANLSKNKRLVSEKVGQACCRPIAFDDDLSFLDDNLVYHILRKHSAK

RCGCI,
and (SEQ ID NO: 15)
RGQRGKQRGCVLTAIHLNVTDLGLGYETKEELIFRYCSGSCDAAETTYD

KILANLSKNKRLVSEKVGQACCRPIAFDDDLSFLDDNLVYHILREHSAK

ECGCI.

In an aspect, the invention provides a human GDNF variant comprising an amino acid sequence as shown in SEQ ID NO: 9:

RGQRGKQRGCVLTAIHLNVTDLGLGYETKEELIFRYCSGSCDAAETTY

DKILKNLSRNRRLVSEKVGQACCRPIAFDDDLSFLDDNLVYHILRKHS

AKRCGCI.

The invention further provides an intermediate, useful for preparing a Δ31-N-terminus truncated variant of mature human GDNF. The intermediate comprises the amino acid sequence of SEQ ID NO: 23 RGQRGKQRGCVLTAIHLN-VTDLGLGYETKEELIFRYCSGSCDAAETTYDKIL Xaa$_{84}$ NLSXaa$_{88}$NXaa$_{90}$RLVSEKVGQACCRPIAFDDDL SFLDDNLVYHILRXaa$_{125}$HSAKXaa$_{130}$CGCI (SEQ ID NO: 23), which is extended at the N-terminus with a signal secretion peptide. Numbers of signal secretion peptide sequences can be used herein. Exemplary signal secretion peptide sequences include murine kappa leader signal secretion peptide having a sequence of METDTLLLWVLLL-WVPGSTG (SEQ ID NO: 25), and human growth hormone signal secretion peptide having a sequence of (SEQ ID NO: 32)
MATGSRTSLLLAFGLLCLPWLQEGSA.

Intermediates having these signal secretion peptides can produce the claimed human GDNF variants with increased yield over truncated GDNF constructs having other leader sequences. The disclosed intermediates including signal secretion peptide can thus have an amino acid sequence of (SEQ ID NO: 28)
METDTLLLWVLLLWVPGSTGRGQRGKQRGCVLTAIHLNVTDLGLGYETK

EELIFRYCSGSCDAAETTYDKILKNLSRNRRLVSEKVGQACCRPIAFDD

DLSFLDDNLVYHILRKHSAKRCGCI;
or (SEQ ID NO: 35)
MATGSRTSLLLAFGLLCLPWLQEGSARGQRGKQRGCVLTAIHLNVTDLG

LGYETKEELIFRYCSGSCDAAETTYDKILKNLSRNRRLVSEKVGQACCR

PIAFDDDLSFLDDNLVYHILRKHSAKRCGCI.

The invention provides a pharmaceutical composition, comprising a variant of human GDNF as claimed by the present invention and one or more pharmaceutically acceptable diluents, carriers or excipients. The invention provides a variant of human GDNF for use as a medicament. The invention further provides a variant of human GDNF for use in the treatment of Parkinson's disease. The invention provides a variant of GDNF for use as a therapy.

A variant wherein $Xaa_{84}$ is A, $Xaa_{88}$ is K, and $Xaa_{90}$ is K is preferred.

A variant wherein $Xaa_{84}$ is K, $Xaa_{88}$ is R, and $Xaa_{90}$ is R is preferred.

A variant wherein $Xaa_{125}$ is K and $Xaa_{130}$ is R is preferred.

A variant wherein $Xaa_{84}$ is A, $Xaa_{88}$ is K, and $Xaa_{90}$ is K, $Xaa_{125}$ is E and $Xaa_{130}$ is E is preferred.

DETAILED DESCRIPTION

It has been reported that wild type GDNF binds to heparin and extracellular matrix, likely through the positive charges located in the N-terminal 1-31 amino acid residues, therefore limiting the distribution of GDNF upon delivery in the brain (Lin et al., *J Neurochem* 63, 758-768, 1994; Rickard et al., *Glycobiology* 13, 419-426, 2003; Piltonen et al., *Experimental Neurology* 219, 499-506, 2009). It has also been reported that GDNF provides functional improvements and has neuroprotective actions in rodent and primate models of Parkinson's disease (Tomac et al, 1995; Gash et al., 1996). Wild type GDNF protein from *E. coli* has been administered centrally to patients suffering from Parkinson's disease with mixed results. In two small open labelled studies, GDNF produced long-lasting improvement in motor function (Gill et al., 2003, Slevin et al., 2005). In addition, increased dopaminergic neuron sprouting was evident in one patient who died of unrelated causes—myocardial infarction (Love et al 2005). However, in a randomized, placebo-controlled, Phase IIa trial of 34 patients conducted by Amgen, intra-putamen delivery of GDNF (Liatermin) showed no symptomatic improvement at 6 months (Lang et al., 2006). The claimed GDNF variants exhibit improved properties compared to the previously tested wild type GDNF protein from *E. coli*.

Wild type GDNF full length construct sequence (211aa) containing the signal peptide (the first 19 amino acids, SEQ ID NO: 4), pro-domain (italics, SEQ ID NO: 5), and mature peptide (underlined, SEQ ID NO: 3) is indicated as SEQ ID NO: 1:

MKLWDVVAVCLVLLHTAS*APPLPAGKRPPEAPAEDRSLGRRRAPFALSS*

*DSNMPEDYPDQFDDVMDFIQATIKRLKRSPDKQMAVLPRRERNRQAAAA*

*NPENSRGKGRRGQRGKNRGCVLTAIHLNVTDLGLGYETKEELIFRYCSG*

<u>SCDAAETTYDKILKNLSRNRRLVSDKVGQACCRPIAFDDDLSFLDDNLV</u>

<u>YHILRKHSAKRCGCI</u>.

The wild type GDNF full length DNA sequence is indicated as SEQ ID NO: 2:

ATGAAGCTGTGGGACGTGGTGGCCGTGTGCCTGGTGCTGCTGCACACCG

CCAGCGCTTTCCCACTGCCAGCCGGCAAGAGACCCCCAGAGGCCCCAGC

CGAGGACAGAAGCCTGGGCAGGCGGAGGGCCCCATTCGCCCTGAGCAGC

GACAGCAACATGCCAGAGGACTACCCCGACCAGTTCGACGACGTCATGG

ACTTCATCCAGGCCACCATCAAGAGGCTGAAGAGGTCACCCGACAAGCA

GATGGCCGTGCTGCCCAGGCGGGAGAGGAACAGGCAGGCCGCCGCCGCC

AACCCAGAGAATTCCAGGGGCAAGGGCAGAAGGGGTCAACGGGCAAGA

ACAGGGGCTGCGTGCTGACCGCCATCCACCTGAACGTGACCGACCTGGG

CCTGGGCTACGAGACCAAGGAGGAGCTGATCTTCAGGTACTGCAGCGGC

AGCTGCGACGCCGCCGAGACCACCTACGACAAGATCCTGAAGAACCTGA

GCAGGAACAGGCGGCTGGTCTCCGACAAGGTGGGCCAGGCCTGCTGCAG

GCCCATCGCCTTCGACGACGACCTGAGCTTCCTGGACGACAACCTGGTG

TACCACATCCTGAGGAAGCACAGCGCCAAGAGATGCGGCTGCATC.

The amino acid positions of the variants of the present invention are determined from the 134 amino acid polypeptide of mature human wild type GDNF (SEQ ID NO: 3). Mutations are designated by the original amino acid, followed by the number of the amino acid position, followed by the replacement amino acid. The numerical designation of each variant is based on wild type mature sequence ("mature WT GDNF") before truncation. For example, a substitution for Lys (K) at position 84 (i.e. K84) with Ala (A) is designated as K84A. In a similar fashion, the multiple substitutions for Lys (K) at position 84 with Ala (A), Arg (R) at position 88 with Lys (K), Arg (R) at position 90 with Lys (K) and Asp (D) at position 95 with Glu (E) is designated as K84A/R88K/R90K/D95E. As used herein the abbreviation "KAKKE" refers to K84A-R88K-R90K-D95E.

As used herein, "full length GDNF" refers to the full protein sequence, including signal peptide, prodomain, and mature domain.

As used herein, "mature GDNF" or "full length mature GDNF" refers to the full GDNF mature domain (with signal peptide and prodomain cleaved off).

As used herein, "Δ31-N-terminus truncated GDNF" refers to GDNF mature domain lacking the first 31 amino acids at the N-terminus. As used herein, "Δ31-N-terminus truncated GDNF" and "human GDNF variant" (or "GDNFv") are used interchangeably.

Full length GDNF constructs when transfected in HEK293 cells over 5 days produce predominantly full length mature GDNF. When full length GDNF constructs are transfected in CHO cells over a longer period of time and during stable cell-line generation, truncated forms of GDNF are the predominant forms (Lin et al., *Science* 260, 1130-1132, 1993). Delta31 ("Δ31"), a truncated variant form of mature human GDNF in which amino acid residues number 1 through 31 have been deleted at the N-terminus, has SEQ ID NO: 8, and can be purified from the mixture.

The N-terminus truncated Δ31 GDNF variant can be produced in a mammalian or bacterial expression system by deleting both the prodomain peptide sequence and the first 31 amino acid residues of the mature GDNF peptide at the DNA level, and using a number of secretion signal sequence peptides, such as native GDNF secretion signal peptide (SEQ ID NO: 4: MKLWDVVAVCLVLLHTASA); murine kappa leader secretion signal peptide (SEQ ID NO: 25: METDTLLLWVLLLWVPGSTG); and human growth hormone secretion signal peptide (SEQ ID NO: 32: MATGSRTSLLLAFGLLCLPWLQEGSA). These constructs can produce single species homogenous Δ31-N-terminus truncated GDNF variants.

One of ordinary skill in the art would understand that the claimed GDNF variants do not exclude the possibility of glycosylation. The claimed GDNF variants can be glycosylated as appropriate, depending on the expression system used. For example, mammalian expressed GDNF variants are glycosylated at position N49 while bacterial expressed variants are not.

When full length native sequence construct is used (SEQ ID NO: 2) during expression, a mixture of GDNF species with various N-terminal truncations are produced as well as mature form (non-truncated) with or without the prodomain region.

The following examples, performed essentially as described below, may be used to assess certain characteristics of human GDNF variants of the invention.

EXAMPLE 1

Protein Expression, Purification and Immunogenicity Analysis a. Sub-Cloning, Mutation, Expression, Unfolding, Re-Folding, and Purification of *E. coli*-Expressed GDNFv Sub-Cloning.

*E. coli* strain BL21-CodonPlus (DE3)-RIPL harboring plasmid pET-30a(+)/rhGDNF is grown on Luria-Bertani broth medium containing kanamycin at a final concentration of 30 mg/ml overnight at 37° C. After harvesting the cells by centrifugation the plasmid vector is isolated by using a QIAquick Spin Miniprep kit (Qiagen) following the manufacturer's protocol. The isolated plasmid DNA is then used for primer extension reaction of the Δ31-GDNF and Δ31-N38Q-GDNF genes encoding for Δ31-GDNF protein (31 residues truncated from the N-terminus of mature human GDNF) and Δ31-N38Q-GDNF protein (31 residues truncated from the N-terminus of mature human GDNF in which the aspargine residue at position 38 is substituted by glutamine), respectively. This may be accomplished using the oligonucleotide primers Δ31 for, Δ31-rev, Δ31-N38Q-for, and Δ31-N38Q-rev (SEQ ID NOs:6, 7, 39, and 40, respectively) containing NdeI and XhoI restriction endonuclease sites designed to anneal to the 5' and 3' ends of the gene. The NdeI and XhoI restriction sites introduced at the 5' ends of the sense and antisense primers allow cloning of Δ31-GDNF and Δ31-N38Q-GDNF into the corresponding sites of the vector pET-30a(+). Primer extension reaction is performed for 3 min at 94° C., followed by 16 three-step cycles of 1 min at 94° C., 0.5 min at 55° C., and 1 min at 72° C., with a final 10 min step at 72° C., in a total volume of 100 μl by using 80 ng template DNA, forward and reverse primers, and PCR Supermix (Invitrogen #10572-014). The resulting amplicons are verified on agarose gel electrophoresis and cleaned using QIAquick PCR purification kit (Qiagen) following the manufacturer's protocol.

Both the amplified Δ31-GDNF or Δ31-N38Q-GDNF gene and pET-30a(+) vector are digested for 2 h at 37° C. with NdeI and XhoI, followed by purification of the DNA by agarose gel electrophoresis using the QIAquick Gel Extraction kit. The Δ31-GDNF or Δ31-N38Q-GDNF is then ligated into the pET-30a(+) plasmid using T4 DNA ligase and following the manufacturer's protocol. 2-5 μl of the ligation reaction mixtures is used to transform directly 50-100 μl of *E. coli* strain BL21-CodonPlus (DE3)-RIPL chemically competent cells following the manufacturer's protocol (Agilent #230280). The resulting transformant colonies obtained by plating on Luria-Bertani agar plates containing kanamycin at a final concentration of 30 ng/ml are screened for the presence of correct construct through sequencing the extracted plasmid in both directions by using the standard T7 promotor and T7 terminator oligonucleotide primers.

Mutations.

Site-directed mutagenesis is carried out using a QuikChange Multi Site-Directed Mutagenesis kit (Stratagene, La Jolla, Calif.) to prepare Δ31-N38Q-D95E-GDNF and Δ31-N38Q-K84A-R88K-R90K-D95E-GDNF. The method uses Δ31-N38Q-GDNF, inserted into pET-30a(+) as a template, and Δ31-N38Q-D95E-for and Δ31-N38Q-D95E-rev oligonucleotides (Table 1, SEQ ID NOs:41 and 42) as forward and reverse primers, respectively. Subsequently, the successfully mutated Δ31-N38Q-D95E gene inserted into pET-30a(+) is used as a template, and 43'-N38Q-K84A-R88K-R90K-D95E-for and Δ31-K84A-R88K-R90K-D95E-rev oligonucleotides (Table 1, SEQ ID NOs:43 and 44) as forward and reverse primers, respectively, to produce Δ31-N38Q-K84A-R88K-R90K-D95E-GDNF. The DNA sequence is confirmed and the plasmid is transformed into *E. coli* strain BL21-CodonPlus (DE3)-RIPL chemically competent cells.

Protein Expression.

Permanent frozen stocks of *E. coli* cells BL21-CodonPlus (DE3)-RIPL harboring plasmid pET-30a(+)/GDNFv are used to inoculate 50 ml of 2×TY broth medium containing kanamycin at final concentrations of 30 μg/ml, at 37° C. After 9 h, 5 ml of the starter culture is used to inoculate 6×2 liters of the same liquid culture medium at 37° C. When the culture reaches an optical density at 600 nm between 0.8 and 1.4, typically after 16 h, IPTG is added to a final concentration of 1 mM and the temperature of the culture is lowered between 27 and 30° C. for 5 h. Cells are harvested by centrifugation at 10,000 g for 20 min at 4° C. and stored at −80° C.

Solubilization-Re-Folding.

The cell paste is suspended in 2-3 volumes of a solution of 0.2 mg/ml lysozyme, 5 mM $MgCl_2$ and 50 mM Tris-Cl at pH 8 and allowed to incubate with stirring for 30 min on ice. The resulting slurry is sonicated on ice for 10 min (5 sec pulses, 2 sec interval, 30-40% amplitude). Thereafter, GDNFv is recovered in the form of inclusion bodies which are isolated from cell lysate by centrifugation at 20,000 g for 20 min and solubilized in 4M guanidine, 90 mM cysteine, 20 mM Tris-Cl, pH 8.5. The protein is re-folded to the active form by 10× dilution with 0.2 M guanidine, 2M urea, 20 mM Tris-Cl, pH 8.75. The refold mixture is held at 4° C. for 2 days.

Purification.

The refolded GDNFv is purified to homogeneity through 3-steps of column chromatography:
 1. Cation Exchange Chromatography (CEX) on SP column
 2. Hydrophobic Interaction Chromatography (HIC) on Phenyl column
 3. Size Exclusion Chromatography (SEC) on Superdex-75 column.

The re-natured protein is firstly applied to an SP Sepharose fast flow column equilibrated in 20 mM sodium acetate, pH 5. GDNFv is eluted with an ascending linear salt gradient from 0.3 to 1 M NaCl in 20 mM sodium acetate, pH 5. The CEX mainstream pool is supplemented with NaCl to a final concentration of 2.5 M and then applied to a Phenyl Sepharose HP hydrophobic interaction chromatography column in 20 mM sodium citrate, pH 5. The HIC column is eluted with a descending linear salt gradient from 2.5 to 0 M NaCl in 20 mM sodium citrate, pH 5. GDNFv binds tightly to HIC column. The HIC mainstream pool is then concentrated and finally applied to a Superdex-75 column and the protein is eluted with PBS, pH 7.4. The final pool is concentrated, filtered through a 0.22 micron membrane and stored at −80° C.

b. Expression and Purification of GDNFv in Mammalian Cells

Genes encoding GDNF variants may be prepared using standard molecular biology techniques or by gene synthesis in a CMV promoter driven mammalian expression vector. The recombinant plasmids are used to transiently transfect human embryonic kidney 293EBNA (HEK293) cells and media is harvested after 5 days. In another method, stable Chinese hamster ovary (CHO) cell lines are generated to express GDNF variants. Genes coding for the variant proteins are subcloned into the Glutamine Synthetase (GS)-containing expression plasmid backbones (pEE12.4-based plasmids, Lonza Biologics, Slough, UK) in frame with the native GDNF signal sequence with pro-domain according to the manufacturer's instructions. Full length GDNF constructs (SEQ ID NO: 2) in pEE12.4 based vectors are transfected in CHO and produce truncated forms of GDNF where Δ31 is the predominant forms and can be purified from the mixture. When the pro-domain and the first N-terminus 31 amino acids are removed, then the 431-N-terminus truncated GDNF variant is produced efficiently and cleanly in a mammalian expression system without the need for purification from a mixture of full length and truncated products as reported previously. The native GDNF secretion signal peptide may also be replaced with numbers of secretion signal peptides, including murine kappa leader secretion signal peptide or human growth hormone secretion signal peptide. The Δ31-N-terminus truncated GDNF variant is still produced efficiently and cleanly with all the disclosed secretion signal peptides but with variable levels of expression. GDNF variants incorporating desired mutations are subcloned into suitable expression vectors (such as pEMK-NF2, Lonza) in frame with the murine kappa signal sequence.

Purification.

GDNFv is purified to homogeneity through 4-step bead chromatography:

1. Cation Exchange Chromatography (CEX) on SP column
2. Hydrophobic Interaction Chromatography (HIC) on Phenyl column
3. Cation Exchange Chromatography (CEX) on multimodel Capto MMC column
4. Size Exclusion Chromatography (SEC) on Superdex-75 column.

Briefly, the harvested culture media containing GDNF variant proteins is firstly applied to an SP Sepharose fast flow column equilibrated in 20 mM sodium acetate, pH 5. GDNFv is eluted with a linear salt gradient from 0 to 1M NaCl in 20 mM sodium acetate, pH 5. The CEX mainstream pool is supplemented with NaCl to a final concentration of 2.5 M and then applied to a Phenyl Sepharose HP hydrophobic interaction chromatography column in 20 mM sodium acetate, pH 5. The HIC column is eluted with a reversed linear salt gradient from 2.5 to 0 M NaCl in 20 mM sodium acetate, pH 5. GDNFv binds weakly to HIC column. A pool of the flow through and early elution fractions is then applied to the multimodel resin of Capto MMC column at pH 5. The column is washed with 50 mM Tris-Cl, pH 8, and then GDNFv is eluted with a linear salt gradient from 0 to 1 M NaCl in 50 mM Tris-Cl, pH 8. The Capto MMC mainstream is finally applied to a Superdex-75 column and the protein is eluted with PBS, pH 7.4. The final pool is filtered through a 0.22 micron membrane and stored at 2-8° C.

TABLE 1

Oligonucleotide Primers Used for PCR and Site-directed Mutagenesis

| Primer | Nucleotide sequence | Purpose |
| --- | --- | --- |
| Δ31-for[a] | 5'TATA*CATATG*CGTGGACAACGTGGTAAAAACCGTGGTTGTGTGCTG-3' (SEQ ID No: 6) | PCR |
| Δ31-rev[a] | 5'-GGTG*CTCGAG*TTATTAAATGCAGCCGCAACGTTTCGCGCT-3' (SEQ ID No: 7) | PCR |
| Δ31-N38Q-for[a,b] | 5'-TATACATATGCGTGGACAACGTGGTAAA<u>CAA</u>CGTGGTTGTGTGCTG-3' (SEQ ID No: 39) | PCR |
| Δ31-N38Q-rev[a] | 5'-GGTG*CTCGAG*TTATTAAATGCAGCCGCAACGTTTCGCGCT-3' (SEQ ID No: 40) | PCR |
| Δ31-N38Q-D95E-for[b] | 5'-GTCTGGTGAGCG<u>A</u>GAAAGTGGGTCAG-3' (SEQ ID No: 41) | Mutagenesis |
| Δ31-N38Q-D95E-rev[b] | 5'-CTGACCCACTTT<u>C</u>TCGCTCACCAGAC-3' (SEQ ID No: 42) | Mutagenesis |
| Δ31-N38Q-KAKKE-for[b] | 5'-CCTATGATAAAATCCTGG<u>C</u>AAACCTGAGC<u>AA</u>GAAC<u>AAA</u>CGTCTGG TGAGCGAGAAAG-3' (SEQ ID No: 43) | Mutagenesis |
| Δ31-N38Q-KAKKE-rev[b] | 5'-CTTTCTCGCTCACCAGACG<u>TTT</u>GTT<u>CTT</u>GCTCAGGTTT<u>GC</u>CAGGAT TTTATCATAGG-3' (SEQ ID No: 44) | Mutagenesis |

[a]Endonuclease restriction sites or NdeI and XhoI enzymes are italicized.
[b]Underlined letters indicate mismatches.

Epivax Analysis of Immunogenicity Potential

Selected human GDNF variants with a reduced probability of binding HLA-DR are made (SEQ ID NOs: 12 and 15) and compared to wild type GDNF in the GFRα and heparin binding assay.

EXAMPLE 2

Stability of GDNF Wildtype and Δ31 GDNF Variant

The stability of the full length mature GDNF wildtype and the Δ31-N-terminus truncated GDNF variants may be assessed using a number of analytical techniques such as RP-HPLC, SE-HPLC, Cation Exchange HPLC, and mass spectrometry to identify any degradation sites in these molecules. Mutations are then made to remove the chemical degradation sites to improve stability of human GDNF variant.

Analytical Reverse Phase Chromatography (RP-HPLC).

On Zorbax $C_8$ SB-300 Å, 3.5 micron, 4.6×50 mm column heated at 60° C. (Agilent Technologies #865973-909). Mobile phase is 0.1% TFA in $H_2O$. GDNFv elutes as a single peak at 214 nm with a retention time of 19-20 min by a linear acetonitrile gradient from 5 to 50% over 30 min at a flow rate of 1 ml/min for 35 min.

Analytical Size Exclusion Chromatography (SEC-HPLC).

On TSK-G-2000-SW-XL, 5 micron, 7.8×300 mm column (TOSOH BIOSEP #08540). Mobile phase: PBS+350 mM NaCl, pH 7.4, at a flow rate of 0.5 ml/min for 35 min. GDNFv elutes as a single peak at 214 nm with a retention time of ~16-17 min.

Analytical Cation Exchange Chromatography (CEX-HPLC).

On Dionex, Propac WCX-10, 4×250 mm column (Dionex #054993). Mobile phase is 20 mM sodium Phosphate, 10% acetonitrile, pH 7. GDNFv elutes as a complex peak with a retention time of 25-30 min by a linear salt gradient from 0.15 to 0.6 M NaCl over 45 min with a flow rate of 1 ml/min for 52 min.

Chemical Stability Analysis (LC-MS) of Wild Type (Full Length Bacterial GDNF) Vs Wild Type CHO GDNFv (N-Terminus Δ31 Truncated GDNF).

Wild type (full length bacterial GDNF) vs wild type CHO GDNFv (N-terminus Δ31 truncated GDNF) are stressed at 37° C. for 4 weeks to identify amino acids that may be associated with chemical instability.

Samples

1—WT *E. coli* full length GDNF at 4° C. for 4 weeks, 1.0 mg/mL
2—WT *E. coli* full length GDNF at 37° C. for 4 weeks, 1.0 mg/mL
3—WT CHO Δ31-GDNFv at 4° C. for 4 weeks, 1.0 mg/mL
4—WT CHO Δ31-GDNFv at 37° C. for 4 weeks, 1.0 mg/mL Intact and Partially Molecular Analysis.

A 10 μL aliquot of each sample (solution is mixed with 20 μL of water or 10 μL aliquot of each solution) is mixed with 40 μL of 100 mM tris-HCl buffer, pH8, 1.0 μL of 50 mg/mL DTT at ambient temperature for 30 min. Each sample is submitted for LC/MS analysis.

Lys-C Digest.

A 20 μL aliquot of each sample solution is lyophilized to dryness under speed vacuum system and the material is then reconstituted in 0.5 μL of 50 mg/mL DTT and 4.5 μL of 6 M guanidine-HCl, 0.5 M tris-HCl buffer, pH 8. The mixture is incubated at 37° C. for 30 minutes and each solution is then diluted with 93 μL of water and treated with 2 μL of 0.2 mg/mL Lys-C (Wako) at 37° C. for 2 hours. For CHO GDNFv, 30 μL of the tryptic digest is treated with 0.5 μL of PNGase F at 37° C. for 1 hour (to assess the carbohydrate profile). The digest is acidified with 2 μL of 10% TFA in $H_2O$ before LC/MS analysis.

LC/MS Analysis.

The sample solutions are analyzed by a Waters SYNAPT mass spectrometry coupled with a Waters Acquity UPLC or a Water LCT premier mass spectrometry coupled with a Waters 2795 HPLC.

Top-Down Analysis.

The cleavage products for wild type GDNF are obtained by LC-MS analysis for partially reduced GDNF. Multiple cleavage products are identified and quantitative data for those cleavages are showed on Table 2. Several cleavages (cleavages between N15/R16, N22/P23, N25/526, and N38/R39) have similar degradation pathways as deamidation through succinimide formation. For wild type CHO Δ31-GDNFv, the first 31 amino acid residues are cleaved from the N-terminus Although CHO GDNFv has two potential N-glycosylation sites per chain, only one site is N-glycosylated. Major glycans observed are di- or tri-antennary oligosaccharides with different galactosylation. Interestingly, no significantly sialylated glycans are detected. (Table 3)

Bottom-Up Analysis (Peptide Mapping).

UV chromatograms of Lys-C digest of reduced GDNF stability samples show that, with the exception of GDNF peptide 126-129, all the expected peptides are detected. For CHO material, N-terminal peptides (before R32) are not detected. Peptide 38-60 containing N49 is glycosylated and more than 95% of Asn49 is occupied. Peptide 85-96 containing N85 is not glycosylated. These results are consistent with LC/MS analysis for reduced GDNF samples.

Overall, homo dimer for both wild type and CHO materials is the major component. The minor component, which elutes early, is monomer. According to mass spectroscopy analysis, GDNF Cys41 forms a disulfide bond with a free Cys residue for the monomer. Relative percent for the monomer peaks is very low, and they are <1% for CHO and <0.5% for the wild type by ultraviolet analysis. The monomer content is not changed for the stressed materials.

The degradations, such as oxidation, deamidation and isomerization, are also obtained from the peptide mapping. The results are shown in Table 4. Wild type full length GDNF from *E. coli*. contains two Met residues, M(−1) and M6, and oxidation for those sites are relatively low. GDNF does not contain any Trp residue. GDNF has eight Asp residues for the full length monomer. The major deamidation sites are N25 and N38. Since deamidation occurs much faster at high pH buffer, relative percentage for those sites should be low when stressed in pH 5 or 6 buffer. One isomer peptide, 85-96, is identified but it is not clear due to isomerization of Asp to Iso-Asp or racemization of amino acid residue. It is well-known that high pH stress is generally racemization and low pH stress is Asp isomerization. For wild type full length GDNF, several peptides show the different masses for both the control (4° C.) and stressed (37° C.) samples. They are most likely mis-incorporation during *E. coli*. biosynthesis.

TABLE 2

Relative Percent of GDNFs Cleavage.

| GDNF Peptides | WT- E. coli GDNF 4 weeks, 4° C. | WT- E. coli GDNF 4 weeks, 37° C. | CHO-Δ31-GDNFv 4 weeks, 37° C. |
|---|---|---|---|
| Met + 1-134 | 90.9 | 57.6 | NA |
| 1-134 | 2.8 | 4.1 | NA |
| 2-134 | 2.5 | 4.2 | NA |
| 3-134 | <0.5 | 1.5 | NA |
| 7-134 | 0.5 | 2.4 | NA |
| 16-134 | <0.5 | 2.9 | NA |
| Pyro E17, 17-134 | <0.5 | 2.9 | NA |
| 18-134 | 0.6 | 2.0 | NA |
| 19-134 | 1.7 | 4.1 | NA |
| 20-134 | <0.5 | 3.8 | NA |
| 26-134 | <0.5 | 2.7 | NA |
| 32-134 | <0.5 | 2.9 | 97.3 |
| 39-134 | <0.5 | 4.5 | 2.7 |

TABLE 3

CHO-Δ31-GDNFv: Glycans at Glycosylation Site N49

| Glycan Formula at N49 | | | | Relative Percent (%) | |
|---|---|---|---|---|---|
| NeuAc | HexNAc | Hex | Fc | 4° C. for 4 weeks | 37° C. for 4 weeks |
| 0 | 2 | 3 | 0 | 0.5 | 0.5 |
| 0 | 2 | 3 | 1 | 4.3 | 4.4 |
| 0 | 3 | 3 | 0 | 1.9 | 2.2 |
| 0 | 3 | 3 | 1 | 15.1 | 14.8 |
| 0 | 4 | 3 | 0 | 1.8 | 1.5 |
| 0 | 3 | 4 | 1 | 2.6 | 3.1 |
| 0 | 4 | 3 | 1 | 9.4 | 10.0 |
| 0 | 5 | 3 | 0 | 1.3 | 1.5 |
| 0 | 4 | 4 | 1 | 3.4 | 3.5 |
| 0 | 5 | 3 | 1 | 6.6 | 7.0 |
| 0 | 4 | 5 | 1 | 6.3 | 6.5 |
| 0 | 5 | 4 | 1 | 3.4 | 3.7 |
| 0 | 6 | 3 | 1 | 1.3 | 1.4 |
| 0 | 5 | 5 | 1 | 4.0 | 4.5 |
| 0 | 5 | 6 | 0 | 3.4 | 3.1 |
| 0 | 6 | 4 | 1 | 1.5 | 1.5 |
| 0 | 5 | 6 | 1 | 22.5 | 20.9 |
| 0 | 6 | 7 | 0 | 0.7 | 0.6 |
| 0 | 6 | 7 | 1 | 5.1 | 4.6 |
| 0 | 7 | 8 | 1 | 0.5 | 0.8 |
| Aglycosylation at N49 | | | | 4.3 | 4.1 |

TABLE 4

LC-MS Peptide Mapping.

| | Relative Percent (%) | | | |
|---|---|---|---|---|
| | WT-E. coli GDNF | | CHO-Δ31-GDNFv | |
| Residue/Peptides | 4° C., 4 weeks | 37° C., 4 weeks | 4° C., 4 weeks | 37° C., 4 weeks |
| Oxidation | | | | |
| Met(−1) | 1.4 | 2.5 | na[a] | na[a] |
| Met6 | 6.4 | 11.2 | na[a] | na[a] |
| Deamidation | | | | |
| N15/N25, Major N25 | 2.8 | 61.5 | na | na |
| N38 | 1.9 | 20.3 | 6.7 | 27.6 |
| N89 | <0.5 | 4.0 | 1.2 | 3.5 |
| Isomerization | | | | |
| GDNF Peptide 85-96 | <0.5 | 14.4 | 3.6 | 17.7 |

[a]Not available.

These data indicate that the Δ31-N-terminus truncated GDNF variant produced in CHO cells has improved chemical stability due to the deletion of the first 31 amino acid residues that include significant oxidation and deamidation hot spots, as compared with the E. coli-produced full length wild type mature human GDNF when stressed for 4 weeks at 37° C. Further, as shown in Table 5, significant improvement in the biophysical and biochemical properties of two mutated Δ31-N-terminus truncated GDNF variants (N38Q and D95E, respectively) was observed after mutation as compared to either the full length wild type E. coli GDNF or the Δ31-N-terminus truncated GDNF variant before mutation.

TABLE 5

Improved Biophysical and Biochemical Properties of GDNF Variants vs Wild Type GDNF After 4 Weeks Incubation at 37° C. Relative to the 4° C. samples

| | WT-E. coli GDNF- (SEQ ID NO: 3) | | CHO-Δ31-GDNFv (SEQ ID NO: 8) | | CHO-Δ31-N38Q-D95E-GDNFv (SEQ ID NO: 9) | | CHO-Δ31-N38Q-K84A-R88K-R90K-D95E-GDNFv (SEQ ID NO: 12) | |
|---|---|---|---|---|---|---|---|---|
| | 4° C. | 37° C. | 4° C. | 37° C. | 4° C. | 37° C. | 4° C. | 37° C. |
| A-High Molecular Weight Aggregate % (SEC) | | | | | | | | |
| a-0.5 mg/ml | na | na | 1.2% | 2.7% | 0.7% | 1.4% | 0.9% | 1.7% |
| b-0.1 mg/ml | na | na | <2% | <2% | <2% | <2% | <2% | <2% |
| d-15 mg/ml | na | na | 0.68% | na | 0.43% | na | 0.47% | na |
| e-15 mg/ml (3 freeze/thaw) | na | na | 0.66% | na | 0.41% | na | 0.43% | na |

TABLE 5-continued

Improved Biophysical and Biochemical Properties of GDNF Variants vs Wild
Type GDNF After 4 Weeks Incubation at 37° C. Relative to the 4° C. samples

| | WT-E. coli GDNF- (SEQ ID NO: 3) | | CHO-Δ31- GDNFv (SEQ ID NO: 8) | | CHO-Δ31- N38Q- D95E- GDNFv (SEQ ID NO: 9) | | CHO-Δ31- N38Q-K84A- R88K-R90K- D95E- GDNFv (SEQ ID NO: 12) | |
|---|---|---|---|---|---|---|---|---|
| | 4° C. | 37° C. | 4° C. | 37° C. | 4° C. | 37° C. | 4° C. | 37° C. |
| B-Chemical Degradation (RP, % of non main peak) | | | | | | | | |
| a-0.5 mg/ml | na | na | 4.3% | 5.7% | 0.3% | 1.5% | 0% | 1.9% |
| b-0.1 mg/ml | na | na | na | >90% | na | >90% | na | >90% |
| C-Chemical Stability and Modification (CEX, % of main peak) | | | | | | | | |
| a-0.5 mg/ml | na | 8% | 82.3% | 30% | 86% | 57% | 90% | 62% |
| b-0.1 mg/ml | na | na | na | <30% | na | 55% | na | 53% |
| D-N-terminal Clipping (LC-MS mature GDNF peptide sequence, 1 mg/ml) | | | | | | | | |
| a-Met-1-134 | 91% | 58% | na | na | na | na | na | na |
| b-1-134 | 2.8% | 4.1% | na | na | na | na | na | na |
| c-32-134 | <0.5% | 3.0% | 98.2% | 92.8% | 99.6% | 96.0% | 98.4% | 94.9% |
| d-33-134 | na | na | 1.8% | 3.3% | 0.4% | 2.1% | 1.5% | 3.2% |
| e-34-134 | na | na | 0.0% | 1.8% | 0.0% | 1.9% | 0.1% | 1.9% |
| f-39-134 | na | na | 0.0% | 2.1% | 0.0% | 0.0% | 0.0% | 0.0% |
| E-Oxidation(LC-MS) | | | | | | | | |
| a-Met (−1) | 1.4% | 2.5% | na | na | na | na | na | na |
| b-Met (6) | 6.4% | 11.2% | na | na | na | na | na | na |
| F-Deamidation (LC-MS) | | | | | | | | |
| a-N15/25 | 2.8% | 61.5% | na | na | na | na | na | na |
| b-N38/Q38 | 1.9% | 20.3% | 3.2% | 25.9% | 0.7% | 0.7% | 0.5% | 0.6% |
| c-N89/N85 | <0.5% | 4% | 1.3% | 2.2% | 1.0% | 1.7% | 1.2% | 1.9% |
| G-Isomerization/Racemization (LC-MS) | | | | | | | | |
| a-peptide 85-96 | <0.5% | 14.4% | 0.9% | 12.0% | 0.0% | 0.2% | 0.1% | 0.8% |
| H-Glycosylation (LC-MS) | | | | | | | | |
| a-N49 Occupancy | na | na | 99.3% | 99.3% | 99.6% | 99.7% | 98.1% | 97.9% |
| b-Sialic Acid (mole/glycan) | na | na | 0.9 | 0.9 | 0.6 | 0.6 | 1.4 | 1.4 |
| c-Di-antennary | na | na | 7.8% | 7% | 10.8% | 10.5% | 9.8% | 9.2% |
| d-Tri-antennary | na | na | 54.9% | 54.5% | 49.5% | 50.9% | 55.9% | 55.8% |
| e-Tetra-antennary | na | na | 37.2% | 38.5% | 38.5% | 37.5% | 33.1% | 33.7% |

Not available (na)

EXAMPLE 3

In Vitro Binding Activities

The following assays demonstrate that certain variants of human GDNF reduce heparin binding while maintaining GFRα1 receptor binding to provide a variety of differential heparin and receptor binding characteristics.

Binding Kinetics of GDNFv to GFRs on Biacore

GDNF variants (GDNFv: N-terminus-Δ31-truncated) may be expressed in E. coli (bacterial) or mammalian cells (CHO cells or HEK293 EBNA cells) and purified as described in Example 1. The primary sequences of the variants remains the same regardless which expression system is used.

A Biacore® 2000 instrument is used to measure the binding kinetics of GDNFv to human and rat GDNF family receptors (GFRα1 and GFRα2). Measurements are performed at 25° C. Samples are dissolved in HBS-EP buffer (150 mM sodium chloride, 3 mM EDTA, 0.005% (w/v) surfactant P-20, pH 7.4). Protein A, Staphylococcus aureus is immobilized on flow cells 1 to 4 of a CM4 sensor chip (GE Healthcare #BR-1005-39) at a level of ~200 response units (RUs) using amine coupling chemistry to capture GFR Fc chimera (Recombinant Human GFRα-1/GDNF Rα-1 Fc Chimera; Recombinant Human GFRα-2/GDNF Rα-2 Fc Chimera; Recombinant Rat GFRα-1/GDNF Rα-1 Fc Chimera; Recombinant Mouse GFRα-2/GDNF Rα-2 Fc Chimera).

Binding is evaluated using multiple cycles. Each cycle consists of the following steps: 1) injection of about 10 μL of GFR at a concentration of ~1.0 μg/mL and a flow rate of 10 μL/min., aiming at a capture of 120-150 RUs; 2) injection of 250 μL of GDNFv at a flow rate of 50 μL/min., in a final concentration rage between 10 nM and 0.04 nM followed by 20 mM. for dissociation; and 3) regeneration using about 30 μL of 10 mM glycine hydrochloride, pH 1.5. Association and dissociation rates for each cycle are evaluated using a "1:1 (Langmuir) binding" model in the BIAevaluation software, version 4.1.

The results are shown in Tables 6-8 below.

TABLE 6

GDNFv: Binding Kinetics and Affinity to Human GFRα-1

| GDNFv | $k_{On}$ (M$^{-1}$s$^{-1}$) | $k_{Off}$(s$^{-1}$) | $K_D$ (pM) |
|---|---|---|---|
| E. Coli-WT-GDNF[a] (SEQ ID NO: 3) | $(6.0 \pm 2.3) \times 10^6$ | $(3.5 \pm 0.8) \times 10^{-4}$ | $64 \pm 23$ |
| E. Coli-Δ31-GDNF (SEQ ID NO: 8) | $(4.2 \pm 1.3) \times 10^6$ | $(1.7 \pm 0.7) \times 10^{-4}$ | $44 \pm 30$ |
| E. coli-Δ31-N38Q-D95E-GDNF (SEQ ID NO: 9) | $(3.9 \pm 1.3) \times 10^6$ | $(1.6 \pm 0.3) \times 10^{-4}$ | $47 \pm 25$ |
| E. Coli-Δ31-N38Q-K84A-R88K-R90K-D95E-GDNF (SEQ ID NO: 12) | $(5.0 \pm 1.8) \times 10^6$ | $(1.6 \pm 0.2) \times 10^{-4}$ | $35 \pm 18$ |
| CHO-Δ31-GDNF (SEQ ID NO: 8) | $(3.8 \pm 1.5) \times 10^6$ | $(0.9 \pm 0.1) \times 10^{-4}$ | $29 \pm 17$ |
| CHO-Δ31-N38Q-D95E-GDNF (SEQ ID NO: 9) | $(4.5 \pm 2.1) \times 10^6$ | $(1.1 \pm 0.2) \times 10^{-4}$ | $30 \pm 14$ |
| CHO-Δ31-N38Q-K84A-R88K-R90K-D95E-GDNF (SEQ ID NO: 12) | $(6.2 \pm 3.2) \times 10^6$ | $(1.4 \pm 0.4) \times 10^{-4}$ | $29 \pm 15$ |

[a]Determined in the presence of 400 mM NaCl.

TABLE 7

GDNFv: Binding Kinetics and Affinity to Human GFRα-2.

| GDNFv | $k_{On}$ (M$^{-1}$s$^{-1}$) | $k_{Off}$(s$^{-1}$) | $K_D$ (pM) |
|---|---|---|---|
| E. Coli-WT-GDNF (SEQ ID NO: 3) | $2.4 \times 10^6$ | $2.6 \times 10^{-4}$ | 100 |
| CHO-Δ31-GDNF (SEQ ID NO: 8) | $5.3 \times 10^6$ | $2.5 \times 10^{-4}$ | 47 |
| CHO-Δ31-N38Q-D95E-GDNF (SEQ ID NO: 9) | $7.6 \times 10^6$ | $3.5 \times 10^{-4}$ | 47 |
| CHO-Δ31-N38Q-K84A-R88K-R90K-D95E-GDNF (SEQ ID NO: 12) | $9.6 \times 10^6$ | $4.2 \times 10^{-4}$ | 44 |

TABLE 8

Binding Kinetics and Affinity of GDNFv to Rat GFRα-1.

| GDNFv | $k_{On}$ (M$^{-1}$s$^{-1}$) | $k_{Off}$(s$^{-1}$) | $K_D$ (pM) |
|---|---|---|---|
| CHO-Δ31-GDNF (SEQ ID NO: 8) | $5.6 \times 10^6$ | $2.4 \times 10^{-4}$ | 44 |
| CHO-Δ31-N38Q-D95E-GDNF (SEQ ID NO: 9) | $9.4 \times 10^6$ | $1.9 \times 10^{-4}$ | 20 |
| CHO-Δ31-N38Q-K84A-R88K-R90K-D95E-GDNF(SEQ ID NO: 12) | $9.9 \times 10^6$ | $2.1 \times 10^{-4}$ | 21 |

Binding of Human GDNF Variants to GFRα1 using ELISA

GDNF wild type and variants are tested in an ELISA assay, in which binding of the GDNF proteins to the plate-bound receptor (GFRα1) is measured. A "no GDNF" condition and/or an "irrelevant protein" condition are used as negative controls.

Each well of a 96-well plate (Greiner 655081 Immunobind ELISA plates) is coated with 70 µl of human GFRα1 (recombinant human GFRα1-Fc chimera, carrier-free) at 1 µg/ml in carbonate buffer, pH 9.6. If an irrelevant receptor is coated, it is an irrelevant Fc chimera and is coated at the same concentration as GFRα1. The plates are sealed and incubated at 4° C. overnight. The wells are aspirated and washed twice with washing buffer (20 mM Tris (hydroxymethyl) aminomethane, pH 7.4, 0.15 M NaCl, 0.1% Tween-20), using an automatic plate washer. The plates are blocked with 200 µl blocking buffer per well (3% Carnation Instant milk in the above washing buffer) for at least 1 hour at room temperature. Plates are washed twice with washing buffer.

GDNF proteins are serially diluted into blocking buffer at an appropriate concentration range, typically beginning at 5 µg/ml and serially diluting 1:10. A no GDNF control is used, which consists of blocking buffer alone. 50 µl of each GDNF solution is added to the GFRα1 coated wells in triplicate. The plates are incubated for 1.5 hours at room temperature. The wells are then washed 3 times with washing buffer.

A 50 µl aliquot of biotinylated anti-human GDNF antibody (R&D Systems, biotinylated goat anti-human GDNF polyclonal antibody, catalog #BAF212) diluted to a concentration of 1 µg/ml in blocking buffer, is added to each well and incubated for 45 minutes at room temperature. The wells are then washed 3 times with washing buffer.

A 50 µl aliquot of horseradish peroxidase-conjugated streptavidin (Jackson ImmunoResearch, catalog #016-030-084), diluted 1:1000 in blocking buffer, is added to each well and incubated for 20-30 minutes at room temperature. Alternatively, a 1:2000 dilution can be used, with an incubation time of 30-90 minutes. The wells are then washed 3 times with washing buffer. 50 µl of chromogenic substrate (i.e., OPD substrate) is added to each well and allowed to develop at room temperature for 2-3 minutes. The reaction is stopped by adding 100 µl of 1N HCl to each well. The absorbance of the wells is read at 490 nm on a Molecular Devices SpectraMax250 plate reader. The average absorbance for the triplicate wells for each condition are determined, and the resulting values are processed for $EC_{50}$ calculation with Graph Pad Prism software to provide a 95% confidence range. Those ranges are summarized in Table 9 below.

Binding of Human GDNF Variants to Heparin using ELISA

GDNF wild type and variants are tested in an ELISA assay, in which binding of the GDNF proteins to plate-bound heparin is measured. A "no GDNF" condition is used as a negative control.

Each well of a 96-well Heparin Binding plate (BD Biosciences Heparin Binding Plates, catalog #354676) is coated with 70 µl of heparin ((mixed molecular weight heparin from Sigma, Heparin Sodium Salt from Porcine Intestinal Mucosa, catalog #H-3149) at 5 µg/ml in PBS. The plates are sealed and incubated at room temperature overnight, protected from light. The wells are aspirated and washed three times with washing buffer, using an automatic plate washer. The plates are blocked with 200 µl blocking buffer per well for 90-120 minutes at 37° C. (plates are sealed during this incubation). Plates are washed twice with washing buffer.

GDNF proteins are serially diluted into blocking buffer at an appropriate concentration range, typically beginning at 5 µg/ml and serially diluting 1:10. A "no GDNF" control, consisting of blocking buffer alone, is used. A 50 µl aliquot of each GDNF solution is added to the heparin coated wells in triplicate. The plates are incubated for 1.5-2 hours at room temperature. The wells are then washed 3 times with washing buffer.

A 50 µl aliquot of biotinylated anti-human GDNF antibody, diluted to a concentration of 1 µg/ml in blocking buffer, is added to each well and incubated for 45 minutes to 1 hour at room temperature. The wells are then washed 3 times with washing buffer.

A 50 µl aliquot of horseradish peroxidase-conjugated streptavidin, diluted 1:1000 in blocking buffer, is added to each well and incubated for 20-30 minutes at room temperature. Alternatively, a 1:2000 dilution can be used, with an incubation time of 30-90 minutes. The wells are then washed 3 times with washing buffer. A 50 µl aliquot of chromogenic substrate (i.e., OPD substrate) is added to each well and allowed to develop at room temperature for 2-3 minutes. The reaction is stopped by adding 100 µl of 1N HCl to each well. The absorbance of the wells is read at 490 nm on a plate reader. The average absorbance for the triplicate wells for each condition are determined, and the resulting values are processed for $EC_{50}$ calculation with Graph Pad Prism software to provide a 95% confidence range. Those ranges are summarized in Table 9 below.

TABLE 9

| Variants | # of Expts. (n) | GFRα1 binding, $EC_{50}$ 95% confidence range | # of Expts. (n) | Heparin binding, $EC_{50}$ 95% confidence range |
|---|---|---|---|---|
| *E. Coli*-WT-GDNF (SEQ ID NO: 3) | 8 | 0.3-0.4 nM | 10 | 0.2-0.4 nM |
| CHO Δ31 GDNF (SEQ ID NO: 8) | 14 | 0.3-0.6 nM | 16 | 2.0-5.0 nM |
| CHO Δ31-N38Q-D95E GDNF (SEQ ID NO: 9) | 4 | 0.3-1.9 nM | 3 | 19.8-41.3 nM |
| CHO Δ31-N38Q-K84A-R88K-R90K-D95E GDNF (SEQ ID NO: 12) | 5 | Could not determine; no max plateau for 4 of 5 expts | 5 | Could not determine; no max plateau for 4 of 5 expts |
| CHO Δ31-N38Q-K84A-R88K-R90K-D95E-K125E-R130E GDNF (SEQ ID NO: 15) | 1 | Little to no binding seen by this ELISA | 1 | Little to no binding seen by this ELISA |

*2 individual experiments are done, no composite

These data show that the deletion of the N-terminal 31 amino acids (variant named "CHO Δ31 GDNF") from the wild type GDNF (named "WT *E. coli* GDNF") can reduce heparin binding significantly (approximately 10-fold) while maintaining GFRα1 receptor binding, and these data further indicate that a variety of differential heparin and receptor binding characteristics can be achieved through additional variants of human GDNF.

EXAMPLE 4

In Vitro Activities

NS-1 Neurite Outgrowth Assay

GDNF activity for neuronal differentiation is assessed using rat Neuroscreen-1 cells (PC12 subclone). The cells are maintained in F-12K basal medium, 12.5% heat inactivated horse serum, 2.5% heat inactivated fetal bovine serum (FBS), 1× GlutaMAX™ (Invitrogen, Cat.#35050061), and 1× Anti-anti (Invitrogen, Cat.#15240) at 37° C., 95% humidity in collagen coated flasks. To measure neurite outgrowth, the Neuroscreen-1 cells are seeded into Collagen 196-well plates at 2200 cells per well in growth medium using only the interior 60 wells. After 24 hours of cell attachment, the medium is removed and new growth medium containing GFRα1-Fc at 1 µg/ml plus GDNF diluted in an 8 point dilution series is added to the plate in either triplicate wells, or six wells per concentration. Medium plus 1 µg/ml GFRα1-Fc is included as a negative control, and medium plus 25 ng/ml neurite growth factor is included as a positive control for cell response in the assay. The plates are incubated for 96 hours at 37° C., 95% humidity and then fixed by adding 45 µl fixative solution to each well and incubating at room temperature for 1 hour. The plates are washed twice with 1× wash buffer from Neurite Outgrowth Hit Kit™ (Cellomics, Cat.#K07-0001-1) and then washed twice with 1× buffer from the kit. The cells are immuno-stained with the neurite outgrowth reagents from the kit according to manufacturer's instructions. The plates are loaded onto Arrayscan Instrument and analyzed using Arrayscan software and Neuronal Profiling algorithm from Cellomics. Data generated by the algorithm is processed for EC50 calculation with Graph Pad Prism software.

Multiple variants are tested for activity in neuronal differentiation and the observed EC50s for each variant are listed in Table 10A.

TABLE 10A

GDNFv: NS-1 Neurite Outgrowth

| GDNFv | Repeats | $EC_{50}$ (95% confidence range) |
|---|---|---|
| *E. Coli*-WT-GDNF (SEQ ID NO: 3) | 3 | 33-200 pM |
| CHO-Δ31-GDNF (SEQ ID NO: 8) | 17 | 42-82 pM |
| CHO-Δ31-N38Q-D95E-GDNF (SEQ ID NO: 9) | 5 | 47-227 pM |
| CHO-Δ31-N38Q-K84A-R88K-R90K-D95E-GDNF (SEQ ID NO: 12) | 5 | 52-384 pM |
| CHO-Δ31-N38Q-K84A-R88K-R90K-D95E-K125E-R130E-GDNF (SEQ ID NO: 15) | 2 | nd[a] |

[a]Not determined due to either low potency or failure to reach maximum plateau.

All GDNF samples tested here have activity in the neurite outgrowth assay, to varying degrees. The dose curves for the Δ31-N38Q-K84A-R88K-R90K-D95E-K125E-R130E variant do not reach a plateau at a maximum dose in the two experiments performed, so an EC50 could not be calculated. The $EC_{50}$ 95% confidence intervals for the other four GDNF variants overlap in range, demonstrating similar levels of activity in this assay.

C-Ret Receptor Phosphorylation

The c-Ret receptor phosphorylation assay can be used to demonstrate the induction of cRet receptor phosphorylation at position Y1016. GDNF activity for c-Ret receptor phosphorylation is assessed in cells from the human neuroblastoma cell line SH-SY5Y (ATCC) which have been stably transfected to over-express human c-Ret. The cells are maintained in Dulbecco's modified Eagle medium (DMEM), 10% FBS, 3 µg/ml Blasticidin. For c-Ret phosphorylation, the cells are seeded at $5\times10^5$ per well into 24-well collagen coated plates in growth medium without Blasticidin and allowed to attach overnight. The medium is changed to low glucose DMEM+0.25% BSA (bovine serum albumin) for 24 hours. Starvation medium is removed, and the cells are treated with GDNF in no glucose DMEM, 0.25% BSA, 1 µg/ml GFRα1-Fc for 30 minutes at 37° C. Each GDNF variant is tested at multiple concentrations. The treatment medium is removed, and the cells are scraped from the plate surface in ice-cold lysis buffer of M-Per Extraction reagent+Protease Inhibitor cocktail, Phosphatase Inhibitor 1, Phosphatase Inhibitor cocktail 2, and Phosphphatase Inhibitor cocktail 3 (Sigma™). The cell suspensions are vortexed to complete lysis, centrifuged at 14,000×g to pellet cell debris, and the supernatant is quantified for protein concentration using the bicinchoninic acid (BCA) assay reagents. For each GDNF lysate, 10 μg protein is separated by 4-12% NuPAGE® Novex® Bis-Tris Gels (Invitrogen, Cat.#NP0322) and transferred PVDF blots. Tyrosine 1016 phospho-Ret is detected with a rabbit polyclonal antibody and goat-anti-rabbit-HRP antibody; and c-Ret is detected with a mouse monoclonal antibody and a goat-anti-mouse-HRP antibody. The blots are developed with the Supersignal West Pico™ (Thermo Scientific, Cat.#34081) reagents and exposed to x-ray film. Five GDNF variants (WT E. coli GDNF, CHO Δ31 GDNF, CHO Δ31-N38Q-D95E GDNF, CHO Δ31-N38Q-K84A-R88K-R90K-D95E GDNF, and CHO Δ31-N38Q-K84A-R88K-R90K-D95E-K125E-R130E GDNF) are tested in no glucose DMEM, 0.25% BSA medium+1 μg/ml GFRα1-Fc for c-Ret phosphorylation activity at four concentrations of 0.8, 2.0, 4.0, 10, 20, 50 and 100 ng/ml. Medium alone, medium+1 μg/ml GFRα1-Fc, and medium+100 ng/ml CHO Δ31 GDNF are also tested as negative controls. Each of the five GDNF variants induce c-Ret phosphorylation with an $EC_{50}$ of 8-15 ng/ml. These data demonstrate that all five GDNF variants induce c-Ret phosphorylation at Y1016 in a dose dependent manner.

As summarized in Table 10B, the engineered Δ31-N-terminus truncated GDNF variants that showed significant improvement in biophysical and biochemical properties (Tables 5, 6, 9, and 10A) maintained optimized biological properties, e.g., comparable GFRα1 receptor binding, decreased heparin binding, and comparable neurite outgrowth, after 4 weeks of incubation at 37° C.

the infusion commences 1 minute later using a pump. A 2 μl bolus of the test GDNF is infused into the left hemisphere over 4 minutes at 0.5 μl/min, and the cannula remains in place for a further 3 minutes once the infusion ceases. Once the cannula has been removed the incision site is closed, a post-operative analgesic administered and the animal allowed to recover in a temperature-controlled cage before transfer to a home cage. Animals are checked post-operatively in accordance with local ethical guidelines. At an appropriate interval following the infusion, the animal is sacrificed, the brain removed and the caudate nuclei accurately dissected, weighed and frozen pending HPLC analysis of dopamine and metabolites.

The frozen tissue is allowed to thaw quickly and is homogenized in 0.5 ml of homogenization buffer (0.1 M perchloric acid (PCA), 0.1 mM Ethylenediaminetetraacetic acid (EDTA), 2.5 mg/L ascorbic acid) before centrifugation at 20,000 g for 15 minutes. The supernatant is removed and filtered through a syringeless filtration device. Analysis of dopamine (DA), dihydroxyphenylacetic acid (DOPAC) and homovanillic acid (HVA) is carried out using HPLC coupled to electrochemical detection. A 20 μl aliquot of each sample is injected and quantified against an external calibration curve (LC4C, BAS, USA). Mobile phase consists of 100 mM $NaH_2PO_4$, 100 mM $H_3PO_4$, 2 mM OSA, 1 mM EDTA, 13% Methanol (MeOH), pH2.8 using a Hypersil BDS (Base Deactivated Silica) (Thermo Scientific, Cat.#28105) 150×3.0 mm C18 3μ particle column at 40° C. Data are collected using Empower chromatography software. A 4-parameter logistic fit is performed on all data prior to expression as ng/g wet weight tissue. The dopamine turnover measure is expressed as (DOPAC+HVA)/DA and comparisons performed with left hemisphere (treated) versus right hemisphere (intact).

TABLE 10B

Bioactivity Comparison of WT-E. coli GDNF and Δ31-N-terminus truncated GDNF variants After 4 Weeks Incubation at 37° C. Relative to the 4° C. samples

| | WT-E. coli GDNF (SEQ ID NO: 3) | | CHO-Δ31-GDNFv (SEQ ID NO: 8) | | CHO-Δ31-N38Q-D95E-GDNFv (SEQ ID NO: 9) | | CHO-Δ31-N38Q-K84A-R88K-R90K-D95E-GDNFv (SEQ ID NO: 12) | |
|---|---|---|---|---|---|---|---|---|
| | 4° C. | 37° C. | 4° C. | 37° C. | 4° C. | 37° C. | 4° C. | 37° C. |
| GFRα-1 (Biacore, $K_d$, pM) | 64 ± 23 | nc | 29 ± 17 | nc | 30 ± 14 | nc | 29 ± 14 | nc |
| GFRα-1 (ELISA, $EC_{50}$, nM) | 0.4 | nc | 0.6 | nc | 0.8 | nc | nd | nd |
| Heparin (ELISA, $EC_{50}$, nM) | 0.3 | 0.4 | 2.7 | 5.1 | 18.0 | nc | nd | nd |
| Neurite Outgrowth ($EC_{50}$ range, pM) | 33-200 | nc | 42-82 | nc | 47-227 | nc | 52-384 | na |

Not available (na);
Not determined (nd); and
No change (nc)

EXAMPLE 5

GDNF Variant Activity in DA Turnover Assays

Male Sprague-Dawley rats are anaesthetized using isoflurane (3% in $O_2$). The head is shaved and sterilized with iodine solution before the animal is positioned on a stereotaxic frame with temperature-controlled mat. The eyes are protected with ophthalmic gel and anaesthesia is maintained using isoflurane (1-2% in $O_2$).

A midline incision is made on the animal's head, the scalp and underlying tissue reflected and the skull dried to visualize bregma. Coordinates for the caudate nucleus are measured from bregma and dural surface for infusion of GDNF. A 28 gauge infusion cannula is slowly lowered to this position, and

TABLE 11

| Variant | Dopamine turnover Treated (left) | Dopamine turnover Intact (right) |
|---|---|---|
| E. coli-WT GDNF (SEQ ID NO: 3) | 0.25 ± 0.025*** | 0.15 ± 0.008 |
| CHO-Δ 31-GDNF (SEQ ID NO: 8) | 0.25 ± 0.016*** | 0.14 ± 0.006 |
| CHO-Δ31-N38Q-D95E-GDNF (SEQ ID NO: 9) | 0.25 ± 0.018*** | 0.13 ± 0.007 |
| CH0-Δ31-N38Q-K84A-R88K-R90K-D95E-GDNF (SEQ ID NO: 12) | 0.20 ± 0.015*** | 0.13 ± 0.012 |

TABLE 11-continued

| Variant | Dopamine turnover Treated (left) | Dopamine turnover Intact (right) |
|---|---|---|
| CHO-Δ31-N38Q-K84A-R88K-R90K-D95E-K125E-R130E-GDNF (SEQ ID NO: 15) | 0.19 ± 0.021** | 0.14 ± 0.011 |

Values are mean ± s.e.m. n = 5 per group
**$p < 0.01$ or
***$p < 0.001$ vs intact side The data demonstrate that each of the GDNF variants named in Table 11 significantly increase dopamine turnover in the treated hemisphere, as compared to the intact hemisphere.

EXAMPLE 6

In Vivo Assays

6-Hydroxy Dopamine (6-OHDA)-Induced Retrograde Lesion Model

Male Sprague-Dawley rats are anaesthetized using isoflurane (3% in O2). The head is shaved and sterilised with iodine solution before the animal is positioned on a stereotaxic frame with temperature-controlled mat. The eyes are protected with ophthalmic gel and anaesthesia is maintained using isoflurane (1-2% in O2).
A midline incision is made on the animal's head, the scalp and underlying tissue reflected and the skull dried to visualize bregma. Coordinates for the caudate nucleus are measured from bregma and dural surface for infusion of Mug 6-Hydroxydopamine (6-OHDA). A 28 gauge infusion cannula is slowly lowered to this position and the infusion commences 1 minute later. A 2 μl bolus of the 6-OHDA is infused into the left hemisphere over 4 minutes at 0.5 μl/min and the cannula remains in place for a further 3 minutes once the infusion ceases.
At 30 minutes following the 6-OHDA infusion the test GDNF is infused using the same protocol. Coordinates for the GDNF infusion are Anterior-Posterior+1.0, LM−2.5, DV−4.5 mm from bregma and dural surface as before.
Once the cannula has been removed the incision site is closed, a post-operative analgesic administered and the animal allowed to recover in a temperature-controlled cage before transfer to a home cage. Animals are checked post-operatively in accordance with local ethical guidelines. At an appropriate interval following the infusion the animal is sacrificed, the brain removed and the caudate nuclei and substantia nigra accurately dissected, weighed and frozen pending HPLC analysis of dopamine and metabolites.
The frozen tissue is allowed to thaw quickly and is homogenized in 0.5 ml of homogenization buffer (0.1M PCA, 0.1 mM EDTA, 2.5 mg/L ascorbic acid) before centrifugation at 20,000×g for 15 minutes. The supernatant is removed and filtered through a syringeless filtration device. Analysis of dopamine (DA), DOPAC and HVA is carried out using HPLC coupled to electrochemical detection. A 20 μl aliquot of each sample is injected and quantified against an external calibration curve. Mobile phase consists of 100 mM $NaH_2PO_4$, 100 mM $H_3PO_4$, 2 mM OSA, 1 mM EDTA, 13% MeOH, pH 2.8 using a BDS Hypersil 150×3.0 mm C18 3μ particle column at 40° C. Data is collected using Empower chromatography software. A 4-parameter logistic fit is performed on all data prior to expression as ng/g wet weight tissue. Comparisons are performed with left hemisphere (treated) versus right hemisphere (intact).

TABLE 12

Caudate nucleus

| Variant | Dopamine (ng/g) Treated (left) | Dopamine (ng/g) Intact (right) | % depletion |
|---|---|---|---|
| Vehicle | 2617.59 ± 526.91*** | 14033.40 ± 408.75 | 81.35 |
| E. coli-WT-GDNF (SEQ ID NO: 3) | 2707.72 ± 725.92*** | 14805.36 ± 536.71 | 81.71 |
| CHO-Δ31-GDNF (SEQ ID NO: 8) | 2023.86 ± 818.03*** | 14456.09 ± 691.53 | 86.00 |
| CHO-Δ31-N38Q-D95E-GDNF (SEQ ID NO: 9) | 2676.57 ± 558.37*** | 14986.15 ± 931.85 | 82.14 |
| CHO-Δ31-N38Q-K84A-R88K-R90K-D95E-GDNF (SEQ ID NO: 12) | 3112.14 ± 717.45*** | 13730.74 ± 1238.50 | 77.33 |

Values are mean ± s.e.m.
n = 8 per group
***$p < 0.001$ vs intact side

TABLE 13

Substantia Nigra

| Variant | Dopamine (ng/g) Treated (left) | Dopamine (ng/g) Intact (right) | % depletion |
|---|---|---|---|
| Vehicle | 571.33 ± 90.65*** | 990.73 ± 134.48 | 42.33 |
| E. Coli-WT-GDNF (SEQ ID NO: 3) | 836.51 ± 97.15**# | 1167.38 ± 62.07 | 28.34 |
| CHO-Δ31-GDNF (SEQ ID NO: 8) | 856.48 ± 75.45**# | 1160.82 ± 100.56 | 26.22 |
| CHO-Δ31-N38Q-D95E-GDNF (SEQ ID NO: 9) | 903.68 ± 52.60*# | 1152.24 ± 115.61 | 21.57 |
| CHO-Δ31-N38Q-K84A-R88K-R90K-D95E-GDNF (SEQ ID NO: 12) | 970.06 ± 108.05## | 1174.45 ± 134.94 | 17.40 |

Values are mean ± s.e.m.
n = 8 per group
*$p < 0.05$,
**$p < 0.01$ or
***$p < 0.001$ vs intact side
$p < 0.05$,
$p < 0.01$ vs vehicle (treated side)

Administration of 6-OHDA into the caudate nucleus results in a significant decrease in dopamine levels in the treated side compared to the intact side (Table 12). A significant deficit is also observed in the substantia nigra (Table 13), which is prevented by administration of GDNF. All variants of GDNF tested here are significantly different from vehicle, comparing treated sides.

Acute Biodistribution in Rat Brain

Male Sprague-Dawley rats are anaesthetized using isoflurane (3% in $O_2$). The head is shaved and sterilised with iodine solution before the animal is positioned on a stereotaxic frame with temperature-controlled mat. The eyes are protected with ophthalmic gel and anaesthesia is maintained using isoflurane (1-2% in $O_2$).

A midline incision is made on the animal's head, the scalp and underlying tissue are reflected and the skull is dried to visualize bregma. Coordinates for the caudate nucleus are measured from bregma and dural surface for infusion of GDNF (Anterior-Posterior+0.5, Lateral Medial−3.0, Dorsal-Ventral−5.5 mm) A 30 gauge infusion cannula is slowly lowered to this position, and the infusion commences 1 minute later (using a pump). A 2 µl bolus of the test GDNF is infused into the left hemisphere over 4 minutes at 0.5 µl/min, and the cannula remains in place for a further 3 minutes once the infusion ceases. Once the cannula has been removed the incision site is closed, a post-operative analgesic is administered, then the animal is allowed to recover in a temperature-controlled cage. At an appropriate interval following the infusion, the animal is sacrificed and the brain removed and frozen pending cryosectioning for immunohistochemistry.

GDNF Immunohistochemistry (IHC) in Rat Brain

Biodistribution of infused GDNF is tested in an immunohistochemistry assay, in which binding of the antibody to the infused antigen (GDNF and GDNF variants) is measured in rat brains. An isotype control antibody is used as a negative control.

Cryosectioning the frozen rat brains begins with trimming the cerebellum while inside a cryostat at −20 degrees C., using a rat brain matrix to make a flat surface. Optimal Cutting Temperature™ (OCT, Sakura or other similar vendors) is placed on a cooled cryostat specimen chuck. As the OCT begins to freeze, the flat caudal surface of the rat brain is placed on the specimen chuck using −20 degrees C. cooled forceps, so that the OCT tacks the brain in place with the rostral-most brain facing away from the specimen chuck. The specimen chuck is placed in the object holder and tighted. After a microtome blade has been inserted into the knife holder, the trimming function on the cryostat is used to discard the olfactory bulbs as well as the cerebrum, rostral to the infusion track. 8 um thick sections are taken at 300 µm intervals and placed on positively charged glass slides. Two or three adjacent interval sections are placed on each glass slide for each rat brain. Slides are then placed into 4% paraformaldehyde at room temperature for 20 minutes and rinsed in tris-buffered saline tween-20 (TBST) washing buffer. Using a staining solution at room temperature, the slides are incubated for 10 minutes with Dual endogenous enzyme block, rinsed with TBST washing buffer, incubated for 15 minutes each of Avidin and Biotin block, washed with TBST washing buffer, blocked with Protein block for 60 minutes and blown off the slide using an air knife. Biotinylated anti-human GDNF or a biotinylated goat IgG is diluted in Antibody Diluent with background reducing agents to 2 µg/ml and incubated on the slide for 60 minutes, then rinsed with TBST washing buffer 3 times. The slides are incubated with labelled streptavidin biotin 2 (LSAB2) (Dako, Cat.#K0609) for 10 minutes and rinsed with TBST washing buffer. The slides are incubated with DAB+ (2 drops of DAB in DAB diluent for 5 minutes, then rinsed with TBST washing buffer, followed by a rinse with distilled water. After slides are removed from the autostainer, they are counterstained with Hematoxylin™ and coverslipped using Cytoseal XYL™ (Stephens Scientific, Cat. #8312-4). Slides are allowed to dry and then analyzed using Aperio XT to quantify biodistribution.

Quantification of Biodistribution of GDNF in Rat Brain

Images of the slides are acquired at the 20× magnification setting on an Aperio ScanScope XT (running v10.00.00.1805 of the Controller software). Meta data about the slides is stored in Aperio's web-based software, Spectrum (v10.0.1346.1806).

Each brain section is manually outlined using Aperio's image viewer software, ImageScope (v10.0.36.1805). For the first study, the whole brain section with the least amount of visible sectioning artifact is outlined. For the second study, the whole brain section closest to the slide label is outlined. Each outlined region is analyzed using Aperio's "Positive Pixel Count" algorithm (v9) [with all the parameters kept at their default settings, except Image Zoom=0.01 and Intensity Threshold WEAK (Upper Limit)=235].

The GDNF distribution area in $mm^2$ for each rat is computed by summing the positive and strong positive areas output from the positive pixel algorithm. A paired Student's t-test is used to determine statistical significance.

TABLE 14

GDNFv: Rat Brain Biodistribution

| GDNFv | Average Area of Distribution ($mm^2$) |
|---|---|
| E. Coli-WT-GDNF (SEQ ID NO: 3) | 7.05 ± 2.92 Experiment 1<br>9.16 ± 4.19 Experiment 2 |
| CHO-Δ31-GDNF (SEQ ID NO: 8) | 16.07 ± 5.69* Experiment 1<br>20.88 ± 6.56** Experiment 2 |
| CHO-Δ31-N38Q-D95E-GDNF (SEQ ID NO: 9) | 17.91 ± 1.47** Experiment 2 |
| CHO-Δ31-N38Q-K84A-R88K-R90K-D95E-GDNF (SEQ ID NO: 12) | 20.86 ± 3.54** Experiment 2 |
| Vehicle (PBS, negative control) | 0.41 ± 0.25 Experiment 1 |
| IgG (negative control) | 0.01 ± 0.03 Experiment 1 |

*For Δ 31, p < 0.003 with respect to vehicle, IgG and E. coli-WT-GDNF,
**Statistically significant with respect to E. coli WT-GDNF, p < 0.05

The ELISA data on heparin binding (Table 9) demonstrate that modifications to the wild type GDNF can reduce heparin binding compared to E. coli-WT GDNF. These data, together with the biodistribution data shown above in Table 14, confirm that variants that decrease heparin binding can result in an increase in biodistribution in the rat brain. N38Q-D95E and N38Q-K84A-R88K-R90K-D95E variants listed in the above table have increased biodistribution compared to E. coli-WT-GDNF.

The novel GDNF variants of the present invention are preferably formulated as pharmaceutical compositions administered by a variety of routes. Most preferably, such GDNF variants are for parenteral or intracranial administration. Such pharmaceutical compositions and processes for preparing same are well known in the art. See e.g., Remington: The Science and Practice of Pharmacy (A. Gennaro, et. al., eds., 19th ed., Mack Publishing Co., 1995).

A therapeutically effective amount is an amount of the novel GDNF variant of the present invention necessary to impart a therapeutic benefit to the patient. It will be understood that the amount of GDNF variant actually administered will be determined by a physician, in light of the relevant circumstances, including the condition to be treated, the chosen route of administration, the actual active agent administered, the age, weight, and response of the individual patient, and the severity of the patient's symptoms.

SEQUENCE LISTING

<SEQ ID NO: 1; PRT1; *Homo sapiens*>
MKLWDVVAVCLVLLHTASAFPLPAGKRPPEAPAEDRSLGRRRAPFALSSDSNMP
EDYPDQFDDVMDFIQATIKRLKRSPDKQMAVLPRRERNRQAAAANPENSRGKGR
RGQRGKNRGCVLTAIHLNVTDLGLGYETKEELIFRYCSGSCDAAETTYDKILKNL
SRNRRLVSDKVGQACCRPIAFDDDLSFLDDNLVYHILRKHSAKRCGCI <SEQ ID NO: 2; DNA; *Homo sapiens*>
ATGAAGCTGTGGGACGTGGTGGCCGTGTGCCTGGTGCTGCTGCACACCGCCA
GCGCTTTCCCACTGCCAGCCGGCAAGAGACCCCAGAGGCCCCAGCCGAGGA
CAGAAGCCTGGGCAGGCGGAGGGCCCCATTCGCCCTGAGCAGCGACAGCAAC
ATGCCAGAGGACTACCCCGACCAGTTCGACGACGTCATGGACTTCATCCAGG
CCACCATCAAGAGGCTGAAGAGGTCACCCGACAAGCAGATGGCCGTGCTGCC
CAGGCGGGAGAGGAACAGGCAGGCCGCCGCCGCCAACCCAGAGAATTCCAG
GGGCAAGGGCAGAAGGGGTCAACGGGCAAGAACAGGGGCTGCGTGCTGAC
CGCCATCCACCTGAACGTGACCGACCTGGGCCTGGGCTACGAGACCAAGGAG
GAGCTGATCTTCAGGTACTGCAGCGGCAGCTGCGACGCCGCCGAGACCACCT
ACGACAAGATCCTGAAGAACCTGAGCAGGAACAGGCGGCTGGTCTCCGACAA
GGTGGGCCAGGCCTGCTGCAGGCCCATCGCCTTCGACGACGACCTGAGCTTC
CTGGACGACAACCTGGTGTACCACATCCTGAGGAAGCACAGCGCCAAGAGAT
GCGGCTGCATC <SEQ ID NO: 3; PRT1; *Homo sapiens*>
SPDKQMAVLPRRERNRQAAAANPENSRGKGRRGQRGKNRGCVLTAIHLNVTDL
GLGYETKEELIFRYCSGSCDAAETTYDKILKNLSRNRRLVSDKVGQACCRPIAFD
DDLSFLDDNLVYHILRKHSAKRCGCI <SEQ ID NO: 4; PRT1; *Homo sapiens*>
MKLWDVVAVCLVLLHTASA <SEQ ID NO: 5; PRT1; *Homo sapiens*>
FPLPAGKRPPEAPAEDRSLGRRRAPFALSSDSNMPEDYPDQFDDVMDFIQATIKRLKR <SEQ ID NO: 6; DNA; Primer>
TATACATATGCGTGGACAACGTGGTAAAAACCGTGGTTGTGTGCTG <SEQ ID NO: 7; DNA; Primer>
GGTGCTCGAGTTATTAAATGCAGCCGCAACGTTTCGCGCT <SEQ ID NO: 8; PRT1; *Homo sapiens*>
RGQRGKNRGCVLTAIHLNVTDLGLGYETKEELIFRYCSGSCDAAETTYDKILKNL
SRNRRLVSDKVGQACCRPIAFDDDLSFLDDNLVYHILRKHSAKRCGCI <SEQ ID NO: 9; PRT1; Artificial Sequence>
RGQRGKQRGCVLTAIHLNVTDLGLGYETKEELIFRYCSGSCDAAETTYDKILKNL
SRNRRLVSEKVGQACCRPIAFDDDLSFLDDNLVYHILRKHSAKRCGCI <SEQ ID NO: 10; DNA; Artificial Sequence>
ATGAAGCTGTGGGACGTGGTGGCCGTGTGCCTGGTGCTGCTGCACACCGCCA
GCGCTTTCCCACTGCCAGCCGGCAAGAGACCCCAGAGGCCCCAGCCGAGGA
CAGAAGCCTGGGCAGGCGGAGGGCCCCATTCGCCCTGAGCAGCGACAGCAAC
ATGCCAGAGGACTACCCCGACCAGTTCGACGACGTCATGGACTTCATCCAGG
CCACCATCAAGAGGCTGAAGAGGTCACCCGACAAGCAGATGGCCGTGCTGCC
CAGGCGGGAGAGGAACAGGCAGGCCGCCGCCGCCAACCCAGAGAATTCCAG
GGGCAAGGGCAGAAGGGGTCAACGGGCAAGCAGAGGGGCTGCGTGCTGAC
CGCCATCCACCTGAACGTGACCGACCTGGGCCTGGGCTACGAGACCAAGGAG
GAGCTGATCTTCAGGTACTGCAGCGGCAGCTGCGACGCCGCCGAGACCACCT
ACGACAAGATCCTGAAGAACCTGAGCAGGAACAGGCGGCTGGTCTCCGAGA
AGGTGGGCCAGGCCTGCTGCAGGCCCATCGCCTTCGACGACGACCTGAGCTT
CCTGGACGACAACCTGGTGTACCACATCCTGAGGAAGCACAGCGCCAAGAGA
TGCGGCTGCATC <SEQ ID NO: 11; PRT1; Artificial Sequence>
MKLWDVVAVCLVLLHTASAFPLPAGKRPPEAPAEDRSLGRRRAPFALSSDSNMP
EDYPDQFDDVMDFIQATIKRLKRSPDKQMAVLPRRERNRQAAAANPENSRGKGR
RGQRGKQRGCVLTAIHLNVTDLGLGYETKEELIFRYCSGSCDAAETTYDKILKNL
SRNRRLVSEKVGQACCRPIAFDDDLSFLDDNLVYHILRKHSAKRCGCI <SEQ ID NO: 12; PRT1; Artificial Sequence>
RGQRGKQRGCVLTAIHLNVTDLGLGYETKEELIFRYCSGSCDAAETTYDKILANL
SKNKRLVSEKVGQACCRPIAFDDDLSFLDDNLVYHILRKHSAKRCGCI <SEQ ID NO: 13; DNA; Artificial Sequence>
ATGAAGCTGTGGGACGTGGTGGCCGTGTGCCTGGTGCTGCTGCACACCGCCA
GCGCTTTCCCACTGCCAGCCGGCAAGAGACCCCAGAGGCCCCAGCCGAGGA
CAGAAGCCTGGGCAGGCGGAGGGCCCCATTCGCCCTGAGCAGCGACAGCAAC
ATGCCAGAGGACTACCCCGACCAGTTCGACGACGTCATGGACTTCATCCAGG
CCACCATCAAGAGGCTGAAGAGGTCACCCGACAAGCAGATGGCCGTGCTGCC
CAGGCGGGAGAGGAACAGGCAGGCCGCCGCCGCCAACCCAGAGAATTCCAG
GGGCAAGGGCAGAAGGGGTCAACGGGCAAGCAGAGGGGCTGCGTGCTGCTGAC

```
CGCCATCCACCTGAACGTGACCGACCTGGGCCTGGGCTACGAGACCAAGGAG
GAGCTGATCTTCAGGTACTGCAGCGGCAGCTGCGACGCCGCCGAGACCACCT
ACGACAAGATCCTGGCCAACCTGAGCAAGAACAAGCGGCTGGTCTCCGAGAA
GGTGGGCCAGGCCTGCTGCAGGCCCATCGCCTTCGACGACGACCTGAGCTTC
CTGGACGACAACCTGGTGTACCACATCCTGAGGAAGCACAGCGCCAAGAGAT
GCGGCTGCATC

<SEQ ID NO: 14; PRT1; Artificial Sequence>
MKLWDVVAVCLVLLHTASAFPLPAGKRPPEAPAEDRSLGRRRAPFALSSDSNMP
EDYPDQFDDVMDFIQATIKRLKRSPDKQMAVLPRRERNRQAAAANPENSRGKGR
RGQRGKQRGCVLTAIHLNVTDLGLGYETKEELIFRYCSGSCDAAETTYDKILANL
SKNKRLVSEKVGQACCRPIAFDDDLSFLDDNLVYHILRKHSAKRCGCI <SEQ ID NO: 15; PRT1; Artificial Sequence>
RGQRGKQRGCVLTAIHLNVTDLGLGYETKEELIFRYCSGSCDAAETTYDKILANL
SKNKRLVSEKVGQACCRPIAFDDDLSFLDDNLVYHILREHSAKECGCI <SEQ ID NO: 16; DNA; Artificial Sequence>
ATGAAGCTGTGGGACGTGGTGGCCGTGTGCCTGGTGCTGCTGCACACCGCCA
GCGCTTTCCCACTGCCAGCCGGCAAGAGACCCCCAGAGGCCCCAGCCGAGGA
CAGAAGCCTGGGCAGGCGGAGGGCCCCATTCGCCCTGAGCAGCGACAGCAAC
ATGCCAGAGGACTACCCCGACCAGTTCGACGACGTCATGGACTTCATCCAGG
CCACCATCAAGAGGCTGAAGAGGTCACCCGACAAGCAGATGGCCGTGCTGCC
CAGGCGGGAGAGGAACAGGCAGGCCGCCGCCGCCAACCCAGAGAATTCCAG
GGGCAAGGGCAGAAGGGGTCAACGGGGCAAGCAGAGGGGCTGCGTGCTGAC
CGCCATCCACCTGAACGTGACCGACCTGGGCCTGGGCTACGAGACCAAGGAG
GAGCTGATCTTCAGGTACTGCAGCGGCAGCTGCGACGCCGCCGAGACCACCT
ACGACAAGATCCTGGCCAACCTGAGCAAGAACAAGCGGCTGGTCTCCGAGAA
GGTGGGCCAGGCCTGCTGCAGGCCCATCGCCTTCGACGACGACCTGAGCTTC
CTGGACGACAACCTGGTGTACCACATCCTGAGGGAGCACAGCGCCAAGGAGT
GCGGCTGCATC <SEQ ID NO: 17; PRT1; Artificial Sequence>
MKLWDVVAVCLVLLHTASAFPLPAGKRPPEAPAEDRSLGRRRAPFALSSDSNMP
EDYPDQFDDVMDFIQATIKRLKRSPDKQMAVLPRRERNRQAAAANPENSRGKGR
RGQRGKQRGCVLTAIHLNVTDLGLGYETKEELIFRYCSGSCDAAETTYDKILANL
SKNKRLVSEKVGQACCRPIAFDDDLSFLDDNLVYHILREHSAKECGCI <SEQ ID NO: 18; DNA; Homo sapiens>
ATGAAGCTGTGGGACGTGGTGGCCGTGTGCCTGGTGCTGCTGCACACCGCCAGCGCT <SEQ ID NO: 19; DNA; Artificial Sequence>
ATGAAGCTGTGGGACGTGGTGGCCGTGTGCCTGGTGCTGCTGCACACCGCCA
GCGCTAGGGGTCAACGGGGCAAGCAGAGGGGCTGCGTGCTGACCGCCATCCA
CCTGAACGTGACCGACCTGGGCCTGGGCTACGAGACCAAGGAGGAGCTGATC
TTCAGGTACTGCAGCGGCAGCTGCGACGCCGCCGAGACCACCTACGACAAGA
TCCTGAAGAACCTGAGCAGGAACAGGCGGCTGGTCTCCGAGAAGGTGGGCCA
GGCCTGCTGCAGGCCCATCGCCTTCGACGACGACCTGAGCTTCCTGGACGAC
AACCTGGTGTACCACATCCTGAGGAAGCACAGCGCCAAGAGATGCGGCTGCATC <SEQ ID NO: 20; PRT1; Artificial Sequence>
MKLWDVVAVCLVLLHTASARGQRGKQRGCVLTAIHLNVTDLGLGYETKEELIF
RYCSGSCDAAETTYDKILKNLSRNRRLVSEKVGQACCRPIAFDDDLSFLDDNLVY
HILRKHSAKRCGCI <SEQ ID NO: 21; DNA; Artificial Sequence>
ATGAAGCTGTGGGACGTGGTGGCCGTGTGCCTGGTGCTGCTGCACACCGCCA
GCGCTAGGGGTCAACGGGGCAAGCAGAGGGGCTGCGTGCTGACCGCCATCCA
CCTGAACGTGACCGACCTGGGCCTGGGCTACGAGACCAAGGAGGAGCTGATC
TTCAGGTACTGCAGCGGCAGCTGCGACGCCGCCGAGACCACCTACGACAAGA
TCCTGGCCAACCTGAGCAAGAACAAGCGGCTGGTCTCCGAGAAGGTGGGCCA
GGCCTGCTGCAGGCCCATCGCCTTCGACGACGACCTGAGCTTCCTGGACGAC
AACCTGGTGTACCACATCCTGAGGAAGCACAGCGCCAAGAGATGCGGCTGCATC <SEQ ID NO: 22; PRT1; Artificial Sequence>
MKLWDVVAVCLVLLHTASARGQRGKQRGCVLTAIHLNVTDLGLGYETKEELIF
RYCSGSCDAAETTYDKILANLSKNKRLVSEKVGQACCRPIAFDDDLSFLDDNLVY
HILRKHSAKRCGCI <SEQ ID NO: 23; PRT1; Artificial Sequence>
RGQRGKQRGCVLTAIHLNVTDLGLGYETKEELIFRYCSGSCDAAETTYDKIL$Xaa_{84}$
NLS$Xaa_{88}$N$Xaa_{90}$RLVSEKVGQACCRPIAFDDDLSFLDDNLVYHILR$Xaa_{125}$HSAK
$Xaa_{130}$CGCI,
wherein:
i) $Xaa_{84}$ is K or A;
ii) $Xaa_{88}$ is R or K;
iii) $Xaa_{90}$ is R or K;
```

SEQUENCE LISTING iv) Xaa$_{125}$ is K or E; and
v) Xaa$_{130}$ is R or E.

<SEQ ID NO: 24; PRT1; Artificial Sequence>
MKLWDVVAVCLVLLHTASARGQRGKQRGCVLTAIHLNVTDLGLGYETKEELIF
RYCSGSCDAAETTYDKILXaa$_{84}$NLSXaa$_{88}$NXaa$_{90}$RLVSEKVGQACCRPIAFDDDLSF
LDDNLVYHILRXaa$_{125}$HSAKXaa$_{130}$CGCI
wherein:
i) Xaa$_{84}$ is K or A;
ii) Xaa$_{88}$ is R or K;
iii) Xaa$_{90}$ is R or K;
iv) Xaa$_{125}$ is K or E; and
v) Xaa$_{130}$ is R or E.

<SEQ ID NO: 25; PRT1; *Mus musculus*>
METDTLLLWVLLLWVPGSTG

<SEQ ID NO: 26; DNA; Mus musculus>
ATGGAGACAGACACACTCCTGCTATGGGTACTGCTGCTCTGGGTTCCAGGATC
TACCGGT <SEQ ID NO: 27; DNA; Artificial Sequence>
ATGGAGACAGACACACTCCTGCTATGGGTACTGCTGCTCTGGGTTCCAGGATC
TACCGGTAGGGGTCAACGGGGCAAGCAGAGGGGCTGCGTGCTGACCGCCATC
CACCTGAACGTGACCGACCTGGGCCTGGGCTACGAGACCAAGGAGGAGCTGA
TCTTCAGGTACTGCAGCGGCAGCTGCGACGCCGCCGAGACCACCTACGACAA
GATCCTGAAGAACCTGAGCAGGAACAGGCGGCTGGTCTCCGAGAAGGTGGGC
CAGGCCTGCTGCAGGCCCATCGCCTTCGACGACGACCTGAGCTTCCTGGACG
ACAACCTGGTGTACCACATCCTGAGGAAGCACAGCGCCAAGAGATGCGGCTG
CATC <SEQ ID NO: 28; PRT1; Artificial Sequence>
METDTLLLWVLLLWVPGSTGRGQRGKQRGCVLTAIHLNVTDLGLGYETKEELIF
RYCSGSCDAAETTYDKILKNLSRNRRLVSEKVGQACCRPIAFDDDLSFLDDNLVY
HILRKHSAKRCGCI <SEQ ID NO: 29; DNA; Artificial Sequence>
ATGGAGACAGACACACTCCTGCTATGGGTACTGCTGCTCTGGGTTCCAGGATC
TACCGGTAGGGGTCAACGGGGCAAGCAGAGGGGCTGCGTGCTGACCGCCATC
CACCTGAACGTGACCGACCTGGGCCTGGGCTACGAGACCAAGGAGGAGCTGA
TCTTCAGGTACTGCAGCGGCAGCTGCGACGCCGCCGAGACCACCTACGACAA
GATCCTGGCCAACCTGAGCAAGAACAAGCGGCTGGTCTCCGAGAAGGTGGGC
CAGGCCTGCTGCAGGCCCATCGCCTTCGACGACGACCTGAGCTTCCTGGACG
ACAACCTGGTGTACCACATCCTGAGGAAGCACAGCGCCAAGAGATGCGGCTG
CATC <SEQ ID NO: 30; PRT1; Artificial Sequence>
METDTLLLWVLLLWVPGSTGRGQRGKQRGCVLTAIHLNVTDLGLGYETKEELIF
RYCSGSCDAAETTYDKILANLSKNKRLVSEKVGQACCRPIAFDDDLSFLDDNLVY
HILRKHSAKRCGCI <SEQ ID NO: 31; PRT1; Artificial Sequence>
METDTLLLWVLLLWVPGSTGRGQRGKQRGCVLTAIHLNVTDLGLGYETKEELIF
RYCSGSCDAAETTYDKILXaa$_{84}$NLSXaa$_{88}$NXaa$_{90}$RLVSEKVGQACCRPIAFDDDLSF
LDDNLVYHILRXaa$_{125}$HSAKXaa$_{130}$CGCI
wherein:
i) Xaa$_{84}$ is K or A;
ii) Xaa$_{88}$ is R or K;
iii) Xaa$_{90}$ is R or K;
iv) Xaa$_{125}$ is K or E; and
v) Xaa$_{130}$ is R or E.

<SEQ ID NO: 32; PRT1; *Homo sapiens*>
MATGSRTSLLLAFGLLCLPWLQEGSA

<SEQ ID NO: 33; DNA; *Homo sapiens*>
ATGGCTACCGGCAGCAGGACCTCTCTGCTGCTGGCCTTCGGCCTGCTGTGCCT
GCCCTGGCTGCAGGAAGGCAGCGCC <SEQ ID NO: 34; DNA; Artificial Sequence>
ATGGCTACCGGCAGCAGGACCTCTCTGCTGCTGGCCTTCGGCCTGCTGTGCCT
GCCCTGGCTGCAGGAAGGCAGCGCCAGGGGTCAACGGGGCAAGCAGAGGGG
CTGCGTGCTGACCGCCATCCACCTGAACGTGACCGACCTGGGCCTGGGCTAC
GAGACCAAGGAGGAGCTGATCTTCAGGTACTGCAGCGGCAGCTGCGACGCCG
CCGAGACCACCTACGACAAGATCCTGAAGAACCTGAGCAGGAACAGGCGGCT
GGTCTCCGAGAAGGTGGGCCAGGCCTGCTGCAGGCCCATCGCCTTCGACGAC
GACCTGAGCTTCCTGGACGACAACCTGGTGTACCACATCCTGAGGAAGCACA

```
                            SEQUENCE LISTING
GCGCCAAGAGATGCGGCTGCATC

<SEQ ID NO: 35; PRT1; Artificial Sequence>
MATGSRTSLLLAFGLLCLPWLQEGSARGQRGKQRGCVLTAIHLNVTDLGLGYET
KEELIFRYCSGSCDAAETTYDKILKNLSRNRRLVSEKVGQACCRPIAFDDDLSFLD
DNLVYHILRKHSAKRCGCI <SEQ ID NO: 36; DNA; Artificial Sequence>
ATGGCTACCGGCAGCAGGACCTCTCTGCTGCTGGCCTTCGGCCTGCTGTGCCT
GCCCTGGCTGCAGGAAGGCAGCGCCAGGGGTCAACGGGGCAAGCAGAGGGG
CTGCGTGCTGACCGCCATCCACCTGAACGTGACCGACCTGGGCCTGGGCTAC
GAGACCAAGGAGGAGCTGATCTTCAGGTACTGCAGCGGCAGCTGCGACGCCG
CCGAGACCACCTACGACAAGATCCTGGCCAACCTGAGCAAGAACAAGCGGCT
GGTCTCCGAGAAGGTGGGCCAGGCCTGCTGCAGGCCCATCGCCTTCGACGAC
GACCTGAGCTTCCTGGACGACAACCTGGTGTACCACATCCTGAGGAAGCACA
GCGCCAAGAGATGCGGCTGCATC <SEQ ID NO: 37; PRT1; Artificial Sequence>
MATGSRTSLLLAFGLLCLPWLQEGSARGQRGKQRGCVLTAIHLNVTDLGLGYET
KEELIFRYCSGSCDAAETTYDKILANLSKNKRLVSEKVGQACCRPIAFDDDLSFLD
DNLVYHILRKHSAKRCGCI <SEQ ID NO: 38; PRT1; Artificial Sequence>
MATGSRTSLLLAFGLLCLPWLQEGSARGQRGKQRGCVLTAIHLNVTDLGLGYET
KEELIFRYCSGSCDAAETTYDKILXaa84NLSXaa88NXaa90RLVSEKVGQACCRPIAF
DDDLSFLDDNLVYHILRXaa125HSAKXaa130CGCI
wherein:
i) Xaa84 is K or A;
ii) Xaa88 is R or K;
iii) Xaa90 is R or K;
iv) Xaa125 is K or E; and
v) Xaa130 is R or E.

<SEQ ID NO: 39; DNA; Primer>
TATACATATGCGTGGACAACGTGGTAAACAACGTGGTTGTGTGCTG

<SEQ ID NO: 40; DNA; Primer>
GGTGCTCGAGTTATTAAATGCAGCCGCAACGTTTCGCGCT

<SEQ ID NO: 41; DNA; Primer>
GTCTGGTGAGCGAGAAAGTGGGTCAG

<SEQ ID NO: 42; DNA; Primer>
CTGACCCACTTTCTCGCTCACCAGAC

<SEQ ID NO: 43; DNA; Primer>
CCTATGATAAAATCCTGGCAAACCTGAGCAAGAACAAACGTCTGGTGAGCGAGAAAG <SEQ ID NO: 44; DNA; Primer>
CTTTCTCGCTCACCAGACGTTTGTTCTTGCTCAGGTTTGCCAGGATTTTATCATAGG SEQ ID NO: 1: AA-Human GDNF wild type full length SEQ ID NO: 2: DNA-Human GDNF wild type full length SEQ ID NO: 3: AA-Human Mature wild type GDNF SEQ ID NO: 4: AA-Human GDNF native secretion signal peptide SEQ ID NO: 5: AA-Human GDNF Pro-domain SEQ ID NO: 6: DNA-Δ31-for Primer SEQ ID NO: 7: DNA-Δ31-rev Primer SEQ ID NO: 8: AA-Variant 1: Delta-31 GDNF SEQ ID NO: 9: AA-GDNF variant 2: Δ31 + N38Q + D95E(clone D9)
protein (103aa)

SEQ ID NO: 10: DNA construct sequence-GDNF variant 2:
Δ31 + N38Q + D95E (clone D9) DNA (pEE12.4)

SEQ ID NO: 11: AA-GDNF variant 2: Δ31 + N38Q + D95E (clone D9)
protein construct (211aa).

SEQ ID NO: 12: AA-GDNF variant 3: Δ31 + N38Q + K84A-
```

SEQUENCE LISTING

R88K-R90K-D95E (clone F2.1) protein sequence (103aa)

SEQ ID NO: 13: DNA construct sequence-GDNF variant 3: Δ31 + N38Q + K84A-R88K-R90K-D95E (clone F2.1) DNA sequence SEQ ID NO: 14: AA-GDNF variant 3: Δ31 + N38Q + K84A-R88K-R90K-D95E (clone F2.1) protein construct (211aa)

SEQ ID NO: 15: AA-GDNF variant 4: Δ31 + N38Q + K84A-R88K-R90K-D95E + K125E + R130E (clone 4.3) protein sequence (103aa):

SEQ ID NO: 16: DNA construct sequence-GDNF variant 4: Δ31 + N38Q + K84A-R88K-R90K-D95E + K125E + R130E (clone 4.3) DNA sequence SEQ ID NO: 17: AA-GDNF variant 4: Δ31 + N38Q + K84A-R88K-R90K-D95E + K125E + R130E (clone 4.3) protein construct SEQ ID NO: 18: DNA-Human GDNF native secretion signal peptide SEQ ID NO: 19: DNA-Native Peptide-Delta-31 N38Q + D95E Construct SEQ ID NO: 20: AA-Native Peptide-Delta-31 N38Q + D95E (122aa):

SEQ ID NO: 21: DNA-Native Peptide-Delta-31 N38Q + K84A-R88K-R90K-D95E

SEQ ID NO: 22: AA-Native Peptide-Delta-31 N38Q + K84A-R88K-R90K-D95E (122aa):

SEQ ID NO: 23: AA-consensus sequence of variants

SEQ ID NO: 24: AA-Native Peptide-consensus sequence of variants

SEQ ID NO: 25: AA-Murine Kappa Leader Secretion Signal Peptide (MKL)

SEQ ID NO: 26: DNA-Murine Kappa Leader Secretion Signal Peptide (MKL)

SEQ ID NO: 27: DNA-MKL-Delta-31 N38Q + D95E Construct

SEQ ID NO: 28: AA-MKL-Delta-31 N38Q + D95E (123aa):

SEQ ID NO: 29: DNA-MKL-Delta-31 N38Q + K84A-R88K-R90K-D95E Construct

SEQ ID NO: 30: AA-MKL-Delta-31 N38Q + K84A-R88K-R90K-D95E (123aa):

SEQ ID NO: 31: AA-Murine Kappa Leader-consensus sequence of variants

SEQ ID NO: 32: AA-Human Growth Hormone Secretion Signal Peptide(hGH)

SEQ ID NO: 33: DNA-Human Growth Hormone Secretion Signal Peptide(hGH)

SEQ ID NO: 34: DNA-hGH-Delta-31 N38Q + D95E Construct

SEQ ID NO: 35: AA-hGH-Delta-31 N38Q + D95E (129aa):

SEQ ID NO: 36: DNA-hGH-Delta-31 N38Q + K84A-R88K-R90K-D95E Construct

SEQ ID NO: 37: AA-hGH-Delta-31 N38Q + K84A-R88K-R90K-D95E (123aa):

SEQ ID NO: 38: AA-hGH-consensus sequence of variants

SEQ ID NO: 39: DNA-Δ31-N38Q-for Primer

SEQ ID NO: 40: DNA-Δ31-N38Q-rev Primer

SEQ ID NO: 41: DNA-Δ31-N38Q-D95E-for Primer

SEQUENCE LISTING

SEQ ID NO: 42: DNA-Δ31-N38Q-D95E-rev Primer

SEQ ID NO: 43: DNA-Δ31-N38Q-KAKKE-for Primer

SEQ ID NO: 44: DNA-Δ31-N38Q-KAKKE-rev Primer

We claim:

1. A human GDNF variant comprising the amino acid sequence of SEQ ID NO: 9:

RGQRGKQRGCVLTAIHLNVTDLGLGYETKEELIFRYCSGSCDAAETTYDKILKNL SRNRRLVSEKVGQACCRPIAFDDDLSFLDDNLVYHILRKHSAKRCGCI.

2. A pharmaceutical composition comprising a human GDNF variant of SEQ ID NO: 9 and one or more pharmaceutically acceptable diluents, carriers or excipients.

* * * * *

UNITED STATES PATENT AND TRADEMARK OFFICE
CERTIFICATE OF CORRECTION

| | | |
|---|---|---|
| PATENT NO. | : 9,243,046 B2 | Page 1 of 1 |
| APPLICATION NO. | : 14/000704 | |
| DATED | : January 26, 2016 | |
| INVENTOR(S) | : Donmienne Doen Mun Leung et al. | |

It is certified that error appears in the above-identified patent and that said Letters Patent is hereby corrected as shown below:

Title Page
On the first page in Column 2, Line 39 delete "GFRa1" and insert -- GFRα1 --, therefor.

Signed and Sealed this
Twenty-first Day of June, 2016

Michelle K. Lee
*Director of the United States Patent and Trademark Office*

SEQUENCE LISTING

<160> NUMBER OF SEQ ID NOS: 44

<210> SEQ ID NO 1
<211> LENGTH: 211
<212> TYPE: PRT
<213> ORGANISM: Homo sapiens

<400> SEQUENCE: 1

```
Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210
```

<210> SEQ ID NO 2
<211> LENGTH: 633
<212> TYPE: DNA
<213> ORGANISM: Homo sapiens

<400> SEQUENCE: 2

```
atgaagctgt gggacgtggt ggccgtgtgc ctggtgctgc tgcacaccgc cagcgctttc      60
ccactgccag ccggcaagag accccagag gccccagccg aggacagaag cctgggcagg     120
cggagggccc cattcgccct gagcagcgac agcaacatgc cagaggacta ccccgaccag     180
```

```
ttcgacgacg tcatggactt catccaggcc accatcaaga ggctgaagag gtcacccgac      240
aagcagatgg ccgtgctgcc caggcgggag aggaacaggc aggccgccgc cgccaaccca      300
gagaattcca ggggcaaggg cagaaggggt caacggggca gaacagggg ctgcgtgctg       360 accgccatcc acctgaacgt gaccgacctg ggcctgggct acgagaccaa ggaggagctg      420
atcttcaggt actgcagcgg cagctgcgac gccgccgaga ccacctacga caagatcctg      480
aagaacctga gcaggaacag gcggctggtc tccgacaagg tgggccaggc ctgctgcagg      540
cccatcgcct tcgacgacga cctgagcttc ctggacgaca acctggtgta ccacatcctg      600
aggaagcaca gcgccaagag atgcggctgc atc                                  633
```

```
<210> SEQ ID NO 3
<211> LENGTH: 134
<212> TYPE: PRT
<213> ORGANISM: Homo sapiens

<400> SEQUENCE: 3

Ser Pro Asp Lys Gln Met Ala Val Leu Pro Arg Arg Glu Arg Asn Arg
1               5                   10                  15

Gln Ala Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
        130
```

```
<210> SEQ ID NO 4
<211> LENGTH: 19
<212> TYPE: PRT
<213> ORGANISM: Homo sapiens

<400> SEQUENCE: 4

Met Lys Leu Trp Asp Val Val Ala Val Cys Leu Val Leu Leu His Thr
1               5                   10                  15

Ala Ser Ala
```

```
<210> SEQ ID NO 5
<211> LENGTH: 58
<212> TYPE: PRT
<213> ORGANISM: Homo sapiens

<400> SEQUENCE: 5

Phe Pro Leu Pro Ala Gly Lys Arg Pro Pro Glu Ala Pro Ala Glu Asp
1               5                   10                  15

Arg Ser Leu Gly Arg Arg Arg Ala Pro Phe Ala Leu Ser Ser Asp Ser
            20                  25                  30

Asn Met Pro Glu Asp Tyr Pro Asp Gln Phe Asp Asp Val Met Asp Phe
```

35                  40                  45
Ile Gln Ala Thr Ile Lys Arg Leu Lys Arg
    50                  55

<210> SEQ ID NO 6
<211> LENGTH: 46
<212> TYPE: DNA
<213> ORGANISM: Artificial Sequence
<220> FEATURE:
<223> OTHER INFORMATION: Synthetic Construct

<400> SEQUENCE: 6
tatacatatg cgtggacaac gtggtaaaaa ccgtggttgt gtgctg            46

<210> SEQ ID NO 7
<211> LENGTH: 40
<212> TYPE: DNA
<213> ORGANISM: Artificial Sequence
<220> FEATURE:
<223> OTHER INFORMATION: Synthetic Construct

<400> SEQUENCE: 7
ggtgctcgag ttattaaatg cagccgcaac gtttcgcgct            40

<210> SEQ ID NO 8
<211> LENGTH: 103
<212> TYPE: PRT
<213> ORGANISM: Homo sapiens

<400> SEQUENCE: 8

Arg Gly Gln Arg Gly Lys Asn Arg Gly Cys Val Leu Thr Ala Ile His
1               5                   10                  15

Leu Asn Val Thr Asp Leu Gly Leu Gly Tyr Glu Thr Lys Glu Glu Leu
            20                  25                  30

Ile Phe Arg Tyr Cys Ser Gly Ser Cys Asp Ala Ala Glu Thr Thr Tyr
        35                  40                  45

Asp Lys Ile Leu Lys Asn Leu Ser Arg Asn Arg Arg Leu Val Ser Asp
    50                  55                  60

Lys Val Gly Gln Ala Cys Cys Arg Pro Ile Ala Phe Asp Asp Asp Leu
65                  70                  75                  80

Ser Phe Leu Asp Asp Asn Leu Val Tyr His Ile Leu Arg Lys His Ser
                85                  90                  95

Ala Lys Arg Cys Gly Cys Ile
            100

<210> SEQ ID NO 9
<211> LENGTH: 103
<212> TYPE: PRT
<213> ORGANISM: Artificial Sequence
<220> FEATURE:
<223> OTHER INFORMATION: Synthetic Construct

<400> SEQUENCE: 9

Arg Gly Gln Arg Gly Lys Gln Arg Gly Cys Val Leu Thr Ala Ile His
1               5                   10                  15

Leu Asn Val Thr Asp Leu Gly Leu Gly Tyr Glu Thr Lys Glu Glu Leu
            20                  25                  30

Ile Phe Arg Tyr Cys Ser Gly Ser Cys Asp Ala Ala Glu Thr Thr Tyr
        35                  40                  45

Asp Lys Ile Leu Lys Asn Leu Ser Arg Asn Arg Arg Leu Val Ser Glu
    50                  55                  60

```
Lys Val Gly Gln Ala Cys Cys Arg Pro Ile Ala Phe Asp Asp Leu
 65                  70                  75                  80

Ser Phe Leu Asp Asp Asn Leu Val Tyr His Ile Leu Arg Lys His Ser
                 85                  90                  95

Ala Lys Arg Cys Gly Cys Ile
            100
```

<210> SEQ ID NO 10
<211> LENGTH: 309
<212> TYPE: DNA
<213> ORGANISM: Artificial Sequence
<220> FEATURE:
<223> OTHER INFORMATION: Synthetic Construct

<400> SEQUENCE: 10

```
aggggtcaac ggggcaagca gaggggctgc gtgctgaccg ccatccacct gaacgtgacc    60
gacctgggcc tgggctacga gaccaaggag gagctgatct tcaggtactg cagcggcagc   120
tgcgacgccg ccgagaccac ctacgacaag atcctgaaga acctgagcag gaacaggcgg   180
ctggtctccg agaaggtggg ccaggcctgc tgcaggccca tcgccttcga cgacgacctg   240
agcttcctgg acgacaacct ggtgtaccac atcctgagga gcacagcgc caagagatgc   300 ggctgcatc                                                          309
```

<210> SEQ ID NO 11
<211> LENGTH: 211
<212> TYPE: PRT
<213> ORGANISM: Artificial Sequence
<220> FEATURE:
<223> OTHER INFORMATION: Synthetic Construct

<400> SEQUENCE: 11

```
Met Lys Leu Trp Asp Val Val Ala Val Cys Leu Val Leu Leu His Thr
  1               5                  10                  15

Ala Ser Ala Phe Pro Leu Pro Ala Gly Lys Arg Pro Pro Glu Ala Pro
                 20                  25                  30

Ala Glu Asp Arg Ser Leu Gly Arg Arg Arg Ala Pro Phe Ala Leu Ser
             35                  40                  45

Ser Asp Ser Asn Met Pro Glu Asp Tyr Pro Asp Gln Phe Asp Asp Val
     50                  55                  60

Met Asp Phe Ile Gln Ala Thr Ile Lys Arg Leu Lys Arg Ser Pro Asp
 65                  70                  75                  80

Lys Gln Met Ala Val Leu Pro Arg Arg Glu Arg Asn Arg Gln Ala Ala
                 85                  90                  95

Ala Ala Asn Pro Glu Asn Ser Arg Gly Lys Gly Arg Arg Gly Gln Arg
            100                 105                 110

Gly Lys Gln Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
            130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Glu Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
```

```
                195                 200                 205
Gly Cys Ile
    210

<210> SEQ ID NO 12
<211> LENGTH: 103
<212> TYPE: PRT
<213> ORGANISM: Artificial Sequence
<220> FEATURE:
<223> OTHER INFORMATION: Synthetic Construct

<400> SEQUENCE: 12

Arg Gly Gln Arg Gly Lys Gln Arg Gly Cys Val Leu Thr Ala Ile His
1               5                   10                  15

Leu Asn Val Thr Asp Leu Gly Leu Gly Tyr Glu Thr Lys Glu Glu Leu
            20                  25                  30

Ile Phe Arg Tyr Cys Ser Gly Ser Cys Asp Ala Ala Glu Thr Thr Tyr
        35                  40                  45

Asp Lys Ile Leu Ala Asn Leu Ser Lys Asn Lys Arg Leu Val Ser Glu
    50                  55                  60

Lys Val Gly Gln Ala Cys Cys Arg Pro Ile Ala Phe Asp Asp Asp Leu
65                  70                  75                  80

Ser Phe Leu Asp Asp Asn Leu Val Tyr His Ile Leu Arg Lys His Ser
                85                  90                  95

Ala Lys Arg Cys Gly Cys Ile
            100

<210> SEQ ID NO 13
<211> LENGTH: 633
<212> TYPE: DNA
<213> ORGANISM: Artificial Sequence
<220> FEATURE:
<223> OTHER INFORMATION: Synthetic Construct

<400> SEQUENCE: 13
atgaagctgt gggacgtggt ggccgtgtgc ctggtgctgc tgcacaccgc cagcgctttc     60
ccactgccag ccggcaagag acccccagag gccccagccg aggacagaag cctgggcagg    120
cggagggccc cattcgccct gagcagcgac agcaacatgc cagaggacta ccccgaccag    180
ttcgacgacg tcatggactt catccaggcc accatcaaga ggctgaagag gtcacccgac    240
aagcagatgg ccgtgctgcc caggcgggag aggaacaggc aggccgccgc cgccaaccca    300
gagaattcca ggggcaaggg cagaaggggt caacggggca agcagagggg ctgcgtgctg    360
accgccatcc acctgaacgt gaccgacctg ggcctgggct acgagaccaa ggaggagctg    420
atcttcaggt actgcagcgg cagctgcgac gccgccgaga ccacctacga caagatcctg    480
gccaacctga gcaagaacaa gcggctggtc tccgagaagg tgggccaggc ctgctgcagg    540
cccatcgcct tcgacgacga cctgagcttc ctggacgaca acctggtgta ccacatcctg    600
aggaagcaca gcgccaagag atgcggctgc atc                                 633

<210> SEQ ID NO 14
<211> LENGTH: 211
<212> TYPE: PRT
<213> ORGANISM: Artificial Sequence
<220> FEATURE:
<223> OTHER INFORMATION: Synthetic Construct

<400> SEQUENCE: 14

Met Lys Leu Trp Asp Val Val Ala Val Cys Leu Val Leu Leu His Thr
```

-continued

```
              1               5                  10                 15
            Ala Ser Ala Phe Pro Leu Pro Ala Gly Lys Arg Pro Pro Glu Ala Pro
                            20                 25                 30

Ala Glu Asp Arg Ser Leu Gly Arg Arg Ala Pro Phe Ala Leu Ser
                         35                 40                 45

Ser Asp Ser Asn Met Pro Glu Asp Tyr Pro Asp Gln Phe Asp Val
                50                 55                 60

Met Asp Phe Ile Gln Ala Thr Ile Lys Arg Leu Lys Arg Ser Pro Asp
            65                 70                 75                 80

Lys Gln Met Ala Val Leu Pro Arg Arg Glu Arg Asn Arg Gln Ala Ala
                            85                 90                 95

Ala Ala Asn Pro Glu Asn Ser Arg Gly Lys Arg Arg Gly Gln Arg
                         100                105                110

Gly Lys Gln Arg Gly Cys Val Leu Thr Ala Ile His Leu Asn Val Thr
                         115                120                125

Asp Leu Gly Leu Gly Tyr Glu Thr Lys Glu Glu Leu Ile Phe Arg Tyr
                         130                135                140

Cys Ser Gly Ser Cys Asp Ala Ala Glu Thr Thr Tyr Asp Lys Ile Leu
            145                150                155                160

Ala Asn Leu Ser Lys Asn Lys Arg Leu Val Ser Glu Lys Val Gly Gln
                            165                170                175

Ala Cys Cys Arg Pro Ile Ala Phe Asp Asp Asp Leu Ser Phe Leu Asp
                         180                185                190

Asp Asn Leu Val Tyr His Ile Leu Arg Lys His Ser Ala Lys Arg Cys
                         195                200                205

Gly Cys Ile
                         210

<210> SEQ ID NO 15
<211> LENGTH: 103
<212> TYPE: PRT
<213> ORGANISM: Artificial Sequence
<220> FEATURE:
<223> OTHER INFORMATION: Synthetic Construct

<400> SEQUENCE: 15

Arg Gly Gln Arg Gly Lys Gln Arg Gly Cys Val Leu Thr Ala Ile His
            1               5                  10                 15

Leu Asn Val Thr Asp Leu Gly Leu Gly Tyr Glu Thr Lys Glu Glu Leu
                            20                 25                 30

Ile Phe Arg Tyr Cys Ser Gly Ser Cys Asp Ala Ala Glu Thr Thr Tyr
                         35                 40                 45

Asp Lys Ile Leu Ala Asn Leu Ser Lys Asn Lys Arg Leu Val Ser Glu
                50                 55                 60

Lys Val Gly Gln Ala Cys Cys Arg Pro Ile Ala Phe Asp Asp Asp Leu
            65                 70                 75                 80

Ser Phe Leu Asp Asp Asn Leu Val Tyr His Ile Leu Arg Glu His Ser
                            85                 90                 95

Ala Lys Glu Cys Gly Cys Ile
                         100

<210> SEQ ID NO 16
<211> LENGTH: 633
<212> TYPE: DNA
<213> ORGANISM: Artificial Sequence
<220> FEATURE:
<223> OTHER INFORMATION: Synthetic Construct
```

<400> SEQUENCE: 16

```
atgaagctgt gggacgtggt ggccgtgtgc ctggtgctgc tgcacaccgc cagcgctttc      60
ccactgccag ccggcaagag accccagag gccccagccg aggacagaag cctgggcagg     120
cggagggccc cattcgccct gagcagcgac agcaacatgc cagaggacta ccccgaccag     180
ttcgacgacg tcatggactt catccaggcc accatcaaga ggctgaagag gtcacccgac     240
aagcagatgg ccgtgctgcc caggcggag aggaacaggc aggccgccgc cgccaaccca     300
gagaattcca ggggcaaggg cagaagggt caacggggca agcagagggg ctgcgtgctg      360
accgccatcc acctgaacgt gaccgacctg ggcctgggct acgagaccaa ggaggagctg     420
atcttcaggt actgcagcgg cagctgcgac gccgccgaga ccacctacga caagatcctg     480
gccaacctga gcaagaacaa gcggctggtc tccgagaagg tgggccaggc ctgctgcagg     540
cccatcgcct tcgacgacga cctgagcttc ctggacgaca acctggtgta ccacatcctg     600
agggagcaca gcgccaagga gtgcggctgc atc                                  633
```

<210> SEQ ID NO 17
<211> LENGTH: 211
<212> TYPE: PRT
<213> ORGANISM: Artificial Sequence
<220> FEATURE:
<223> OTHER INFORMATION: Synthetic Construct

<400> SEQUENCE: 17

```
Met Lys Leu Trp Asp Val Val Ala Val Cys Leu Val Leu Leu His Thr
1               5                   10                  15
Ala Ser Ala Phe Pro Leu Pro Ala Gly Lys Arg Pro Pro Glu Ala Pro
            20                  25                  30
Ala Glu Asp Arg Ser Leu Gly Arg Arg Ala Pro Phe Ala Leu Ser
        35                  40                  45
Ser Asp Ser Asn Met Pro Glu Asp Tyr Pro Asp Gln Phe Asp Asp Val
    50                  55                  60
Met Asp Phe Ile Gln Ala Thr Ile Lys Arg Leu Lys Arg Ser Pro Asp
65                  70                  75                  80
Lys Gln Met Ala Val Leu Pro Arg Arg Glu Arg Asn Arg Gln Ala Ala
                85                  90                  95
Ala Ala Asn Pro Glu Asn Ser Arg Gly Lys Gly Arg Gly Gln Arg
            100                 105                 110
Gly Lys Gln Arg Gly Cys Val Leu Thr Ala Ile His Leu Asn Val Thr
        115                 120                 125
Asp Leu Gly Leu Gly Tyr Glu Thr Lys Glu Glu Leu Ile Phe Arg Tyr
    130                 135                 140
Cys Ser Gly Ser Cys Asp Ala Ala Glu Thr Thr Tyr Asp Lys Ile Leu
145                 150                 155                 160
Ala Asn Leu Ser Lys Asn Lys Arg Leu Val Ser Glu Lys Val Gly Gln
                165                 170                 175
Ala Cys Cys Arg Pro Ile Ala Phe Asp Asp Leu Ser Phe Leu Asp
            180                 185                 190
Asp Asn Leu Val Tyr His Ile Leu Arg Glu His Ser Ala Lys Glu Cys
        195                 200                 205
Gly Cys Ile
    210
```

<210> SEQ ID NO 18

```
<211> LENGTH: 57
<212> TYPE: DNA
<213> ORGANISM: Homo sapiens

<400> SEQUENCE: 18
atgaagctgt gggacgtggt ggccgtgtgc ctggtgctgc tgcacaccgc cagcgct        57

<210> SEQ ID NO 19
<211> LENGTH: 366
<212> TYPE: DNA
<213> ORGANISM: Artificial Sequence
<220> FEATURE:
<223> OTHER INFORMATION: Synthetic Construct

<400> SEQUENCE: 19
atgaagctgt gggacgtggt ggccgtgtgc ctggtgctgc tgcacaccgc cagcgctagg      60
ggtcaacggg gcaagcagag gggctgcgtg ctgaccgcca tccacctgaa cgtgaccgac     120
ctgggcctgg gctacgagac caaggaggag ctgatcttca ggtactgcag cggcagctgc     180
gacgccgccg agaccaccta cgacaagatc ctgaagaacc tgagcaggaa caggcggctg     240
gtctccgaga aggtgggcca ggcctgctgc aggcccatcg ccttcgacga cgacctgagc     300
ttcctggacg acaacctggt gtaccacatc ctgaggaagc acagcgccaa gagatgcggc     360
tgcatc                                                                 366

<210> SEQ ID NO 20
<211> LENGTH: 122
<212> TYPE: PRT
<213> ORGANISM: Artificial Sequence
<220> FEATURE:
<223> OTHER INFORMATION: Synthetic Construct

<400> SEQUENCE: 20

Met Lys Leu Trp Asp Val Val Ala Val Cys Leu Val Leu Leu His Thr
1               5                   10                  15

Ala Ser Ala Arg Gly Gln Arg Gly Lys Gln Arg Gly Cys Val Leu Thr
            20                  25                  30

Ala Ile His Leu Asn Val Thr Asp Leu Gly Leu Gly Tyr Glu Thr Lys
        35                  40                  45

Glu Glu Leu Ile Phe Arg Tyr Cys Ser Gly Ser Cys Asp Ala Ala Glu
    50                  55                  60

Thr Thr Tyr Asp Lys Ile Leu Lys Asn Leu Ser Arg Asn Arg Arg Leu
65                  70                  75                  80

Val Ser Glu Lys Val Gly Gln Ala Cys Cys Arg Pro Ile Ala Phe Asp
                85                  90                  95

Asp Asp Leu Ser Phe Leu Asp Asp Asn Leu Val Tyr His Ile Leu Arg
            100                 105                 110

Lys His Ser Ala Lys Arg Cys Gly Cys Ile
        115                 120

<210> SEQ ID NO 21
<211> LENGTH: 366
<212> TYPE: DNA
<213> ORGANISM: Artificial Sequence
<220> FEATURE:
<223> OTHER INFORMATION: Synthetic Construct

<400> SEQUENCE: 21
atgaagctgt gggacgtggt ggccgtgtgc ctggtgctgc tgcacaccgc cagcgctagg      60
ggtcaacggg gcaagcagag gggctgcgtg ctgaccgcca tccacctgaa cgtgaccgac     120
```

```
ctgggcctgg gctacgagac caaggaggag ctgatcttca ggtactgcag cggcagctgc      180
gacgccgccg agaccaccta cgacaagatc ctggccaacc tgagcaagaa caagcggctg      240
gtctccgaga aggtgggcca ggcctgctgc aggcccatcg ccttcgacga cgacctgagc      300
ttcctggacg acaacctggt gtaccacatc ctgaggaagc acagcgccaa gagatgcggc      360
tgcatc                                                                 366
```

```
<210> SEQ ID NO 22
<211> LENGTH: 122
<212> TYPE: PRT
<213> ORGANISM: Artificial Sequence
<220> FEATURE:
<223> OTHER INFORMATION: Synthetic Construct

<400> SEQUENCE: 22

Met Lys Leu Trp Asp Val Val Ala Val Cys Leu Val Leu Leu His Thr
1               5                   10                  15

Ala Ser Ala Arg Gly Gln Arg Gly Lys Gln Arg Gly Cys Val Leu Thr
            20                  25                  30

Ala Ile His Leu Asn Val Thr Asp Leu Gly Leu Gly Tyr Glu Thr Lys
        35                  40                  45

Glu Glu Leu Ile Phe Arg Tyr Cys Ser Gly Ser Cys Asp Ala Ala Glu
    50                  55                  60

Thr Thr Tyr Asp Lys Ile Leu Ala Asn Leu Ser Lys Asn Lys Arg Leu
65                  70                  75                  80

Val Ser Glu Lys Val Gly Gln Ala Cys Cys Arg Pro Ile Ala Phe Asp
                85                  90                  95

Asp Asp Leu Ser Phe Leu Asp Asp Asn Leu Val Tyr His Ile Leu Arg
            100                 105                 110

Lys His Ser Ala Lys Arg Cys Gly Cys Ile
        115                 120
```

```
<210> SEQ ID NO 23
<211> LENGTH: 103
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (53)..(53)
<223> OTHER INFORMATION: Xaa at position 53 is Lys or Ala
<220> FEATURE:
<221> NAME/KEY: MISC_FEATURE
<222> LOCATION: (57)..(57)
<223> OTHER INFORMATION: Xaa at position 57 is Arg or Lys
<220> FEATURE:
<221> NAME/KEY: MISC_FEATURE
<222> LOCATION: (59)..(59)
<223> OTHER INFORMATION: Xaa at position 59 is Arg or Lys
<220> FEATURE:
<221> NAME/KEY: MISC_FEATURE
<222> LOCATION: (94)..(94)
<223> OTHER INFORMATION: Xaa at position 94 is Lys or Glu
<220> FEATURE:
<221> NAME/KEY: MISC_FEATURE
<222> LOCATION: (99)..(99)
<223> OTHER INFORMATION: Xaa at position 99 is Arg or Glu

<400> SEQUENCE: 23

Arg Gly Gln Arg Gly Lys Gln Arg Gly Cys Val Leu Thr Ala Ile His
1               5                   10                  15

Leu Asn Val Thr Asp Leu Gly Leu Gly Tyr Glu Thr Lys Glu Glu Leu
```

```
                    20                  25                  30

Ile Phe Arg Tyr Cys Ser Gly Ser Cys Asp Ala Ala Glu Thr Thr Tyr
            35                  40                  45

Asp Lys Ile Leu Xaa Asn Leu Ser Xaa Asn Xaa Arg Leu Val Ser Glu
        50                  55                  60

Lys Val Gly Gln Ala Cys Cys Arg Pro Ile Ala Phe Asp Asp Leu
 65                 70                  75                  80

Ser Phe Leu Asp Asp Asn Leu Val Tyr His Ile Leu Arg Xaa His Ser
                85                  90                  95

Ala Lys Xaa Cys Gly Cys Ile
            100
```

<210> SEQ ID NO 24
<211> LENGTH: 122
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (72)..(72)
<223> OTHER INFORMATION: Xaa at position 72 is Lys or Ala
<220> FEATURE:
<221> NAME/KEY: MISC_FEATURE
<222> LOCATION: (76)..(76)
<223> OTHER INFORMATION: Xaa at position 76 is arg or Lys
<220> FEATURE:
<221> NAME/KEY: MISC_FEATURE
<222> LOCATION: (78)..(78)
<223> OTHER INFORMATION: Xaa at position 78 is Arg or Lys
<220> FEATURE:
<221> NAME/KEY: MISC_FEATURE
<222> LOCATION: (113)..(113)
<223> OTHER INFORMATION: Xaa at position 113 is Lys or Glu
<220> FEATURE:
<221> NAME/KEY: MISC_FEATURE
<222> LOCATION: (118)..(118)
<223> OTHER INFORMATION: Xaa at position 118 is Arg or Glu

<400> SEQUENCE: 24

```
Met Lys Leu Trp Asp Val Val Ala Val Cys Leu Val Leu Leu His Thr
 1               5                  10                  15

Ala Ser Ala Arg Gly Gln Arg Gly Lys Gln Arg Gly Cys Val Leu Thr
            20                  25                  30

Ala Ile His Leu Asn Val Thr Asp Leu Gly Leu Gly Tyr Glu Thr Lys
        35                  40                  45

Glu Glu Leu Ile Phe Arg Tyr Cys Ser Gly Ser Cys Asp Ala Ala Glu
    50                  55                  60

Thr Thr Tyr Asp Lys Ile Leu Xaa Asn Leu Ser Xaa Asn Xaa Arg Leu
 65                 70                  75                  80

Val Ser Glu Lys Val Gly Gln Ala Cys Cys Arg Pro Ile Ala Phe Asp
                85                  90                  95

Asp Asp Leu Ser Phe Leu Asp Asp Asn Leu Val Tyr His Ile Leu Arg
            100                 105                 110

Xaa His Ser Ala Lys Xaa Cys Gly Cys Ile
        115                 120
```

<210> SEQ ID NO 25
<211> LENGTH: 20
<212> TYPE: PRT
<213> ORGANISM: Mus musculus

<400> SEQUENCE: 25

```
Met Glu Thr Asp Thr Leu Leu Leu Trp Val Leu Leu Trp Val Pro
1               5                   10                  15

Gly Ser Thr Gly
            20

<210> SEQ ID NO 26
<211> LENGTH: 60
<212> TYPE: DNA
<213> ORGANISM: Mus musculus

<400> SEQUENCE: 26
atggagacag acacactcct gctatgggta ctgctgctct ggttccagg atctaccggt      60

<210> SEQ ID NO 27
<211> LENGTH: 369
<212> TYPE: DNA
<213> ORGANISM: Artificial Sequence
<220> FEATURE:
<223> OTHER INFORMATION: Synthetic Construct

<400> SEQUENCE: 27
atggagacag acacactcct gctatgggta ctgctgctct gggttccagg atctaccggt      60
aggggtcaac ggggcaagca gagggctgc gtgctgaccg ccatccacct gaacgtgacc      120
gacctgggcc tgggctacga gaccaaggag gagctgatct tcaggtactg cagcggcagc      180
tgcgacgccg ccgagaccac ctacgacaag atcctgaaga acctgagcag gaacaggcgg      240
ctggtctccg agaaggtggg ccaggcctgc tgcaggccca tcgccttcga cgacgacctg      300
agcttcctgg acgacaacct ggtgtaccac atcctgagga gcacagcgc caagagatgc      360 ggctgcatc                                                             369

<210> SEQ ID NO 28
<211> LENGTH: 123
<212> TYPE: PRT
<213> ORGANISM: Artificial Sequence
<220> FEATURE:
<223> OTHER INFORMATION: Synthetic Construct

<400> SEQUENCE: 28

Met Glu Thr Asp Thr Leu Leu Leu Trp Val Leu Leu Trp Val Pro
1               5                   10                  15

Gly Ser Thr Gly Arg Gly Gln Arg Gly Lys Gln Arg Gly Cys Val Leu
            20                  25                  30

Thr Ala Ile His Leu Asn Val Thr Asp Leu Gly Leu Gly Tyr Glu Thr
            35                  40                  45

Lys Glu Glu Leu Ile Phe Arg Tyr Cys Ser Gly Ser Cys Asp Ala Ala
        50                  55                  60

Glu Thr Thr Tyr Asp Lys Ile Leu Lys Asn Leu Ser Arg Asn Arg Arg
65                  70                  75                  80

Leu Val Ser Glu Lys Val Gly Gln Ala Cys Cys Arg Pro Ile Ala Phe
                85                  90                  95

Asp Asp Asp Leu Ser Phe Leu Asp Asp Asn Leu Val Tyr His Ile Leu
            100                 105                 110

Arg Lys His Ser Ala Lys Arg Cys Gly Cys Ile
        115                 120

<210> SEQ ID NO 29
<211> LENGTH: 369
<212> TYPE: DNA
<213> ORGANISM: Artificial Sequence
```

```
<220> FEATURE:
<223> OTHER INFORMATION: Synthetic Construct

<400> SEQUENCE: 29
atggagacag acacactcct gctatgggta ctgctgctct gggttccagg atctaccggt      60
aggggtcaac ggggcaagca gaggggctgc gtgctgaccg ccatccacct gaacgtgacc     120
gacctgggcc tgggctacga gaccaaggag gagctgatct tcaggtactg cagcggcagc     180
tgcgacgccg ccgagaccac ctacgacaag atcctggcca acctgagcaa gaacaagcgg     240
ctggtctccg agaaggtggg ccaggcctgc tgcaggccca tcgccttcga cgacgacctg     300
agcttcctgg acgacaacct ggtgtaccac atcctgagga agcacagcgc caagagatgc     360
ggctgcatc                                                              369

<210> SEQ ID NO 30
<211> LENGTH: 123
<212> TYPE: PRT
<213> ORGANISM: Artificial Sequence
<220> FEATURE:
<223> OTHER INFORMATION: Synthetic Construct

<400> SEQUENCE: 30

Met Glu Thr Asp Thr Leu Leu Leu Trp Val Leu Leu Leu Trp Val Pro
 1               5                  10                  15

Gly Ser Thr Gly Arg Gly Gln Arg Gly Lys Gln Arg Gly Cys Val Leu
            20                  25                  30

Thr Ala Ile His Leu Asn Val Thr Asp Leu Gly Leu Gly Tyr Glu Thr
        35                  40                  45

Lys Glu Glu Leu Ile Phe Arg Tyr Cys Ser Gly Ser Cys Asp Ala Ala
    50                  55                  60

Glu Thr Thr Tyr Asp Lys Ile Leu Ala Asn Leu Ser Lys Asn Lys Arg
65                  70                  75                  80

Leu Val Ser Glu Lys Val Gly Gln Ala Cys Cys Arg Pro Ile Ala Phe
                85                  90                  95

Asp Asp Asp Leu Ser Phe Leu Asp Asp Asn Leu Val Tyr His Ile Leu
            100                 105                 110

Arg Lys His Ser Ala Lys Arg Cys Gly Cys Ile
        115                 120

<210> SEQ ID NO 31
<211> LENGTH: 123
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (73)..(73)
<223> OTHER INFORMATION: Xaa at position 73 is Lys or Ala
<220> FEATURE:
<221> NAME/KEY: MISC_FEATURE
<222> LOCATION: (77)..(77)
<223> OTHER INFORMATION: Xaa at position 77 is Arg or Lys
<220> FEATURE:
<221> NAME/KEY: MISC_FEATURE
<222> LOCATION: (79)..(79)
<223> OTHER INFORMATION: Xaa at position 79 is Arg or Lys
<220> FEATURE:
<221> NAME/KEY: MISC_FEATURE
<222> LOCATION: (114)..(114)
<223> OTHER INFORMATION: Xaa at position 114 is Lys or Glu
<220> FEATURE:
<221> NAME/KEY: MISC_FEATURE
<222> LOCATION: (119)..(119)
```

<223> OTHER INFORMATION: Xaa at position 119 is Arg or Glu

<400> SEQUENCE: 31

Met Glu Thr Asp Thr Leu Leu Leu Trp Val Leu Leu Trp Val Pro
1               5                   10                  15

Gly Ser Thr Gly Arg Gly Gln Arg Gly Lys Gln Arg Gly Cys Val Leu
            20                  25                  30

Thr Ala Ile His Leu Asn Val Thr Asp Leu Gly Leu Gly Tyr Glu Thr
        35                  40                      45

Lys Glu Glu Leu Ile Phe Arg Tyr Cys Ser Gly Ser Cys Asp Ala Ala
    50                  55                  60

Glu Thr Thr Tyr Asp Lys Ile Leu Xaa Asn Leu Ser Xaa Asn Xaa Arg
65                  70                  75                  80

Leu Val Ser Glu Lys Val Gly Gln Ala Cys Cys Arg Pro Ile Ala Phe
                85                  90                  95

Asp Asp Asp Leu Ser Phe Leu Asp Asp Asn Leu Val Tyr His Ile Leu
                100                 105                 110

Arg Xaa His Ser Ala Lys Xaa Cys Gly Cys Ile
            115                 120

<210> SEQ ID NO 32
<211> LENGTH: 26
<212> TYPE: PRT
<213> ORGANISM: Homo sapiens

<400> SEQUENCE: 32

Met Ala Thr Gly Ser Arg Thr Ser Leu Leu Ala Phe Gly Leu Leu
1               5                   10                  15

Cys Leu Pro Trp Leu Gln Glu Gly Ser Ala
            20                  25

<210> SEQ ID NO 33
<211> LENGTH: 78
<212> TYPE: DNA
<213> ORGANISM: Homo sapiens

<400> SEQUENCE: 33
atggctaccg gcagcaggac ctctctgctg ctggccttcg gcctgctgtg cctgccctgg     60
ctgcaggaag gcagcgcc                                                  78

<210> SEQ ID NO 34
<211> LENGTH: 387
<212> TYPE: DNA
<213> ORGANISM: Artificial Sequence
<220> FEATURE:
<223> OTHER INFORMATION: Synthetic Construct

<400> SEQUENCE: 34
atggctaccg gcagcaggac ctctctgctg ctggccttcg gcctgctgtg cctgccctgg     60
ctgcaggaag gcagcgccag gggtcaacgg ggcaagcaga ggggctgcgt gctgaccgcc    120
atccacctga acgtgaccga cctgggcctg ggctacgaga ccaaggagga gctgatcttc    180
aggtactgca gcggcagctg cgacgccgcc gagaccacct acgacaagat cctgaagaac    240
ctgagcagga acaggcggct ggtctccgag aaggtgggcc aggcctgctg caggcccatc    300
gccttcgacg acgacctgag cttcctggac gacaacctgg tgtaccacat cctgaggaag    360
cacagcgcca agagatgcgg ctgcatc                                       387

-continued

```
<210> SEQ ID NO 35
<211> LENGTH: 129
<212> TYPE: PRT
<213> ORGANISM: Artificial Sequence
<220> FEATURE:
<223> OTHER INFORMATION: Synthetic Construct

<400> SEQUENCE: 35

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Arg Gly Gln Arg Gly Lys
            20                  25                  30

Gln Arg Gly Cys Val Leu Thr Ala Ile His Leu Asn Val Thr Asp Leu
        35                  40                  45

Gly Leu Gly Tyr Glu Thr Lys Glu Glu Leu Ile Phe Arg Tyr Cys Ser
    50                  55                  60

Gly Ser Cys Asp Ala Ala Glu Thr Thr Tyr Asp Lys Ile Leu Lys Asn
65                  70                  75                  80

Leu Ser Arg Asn Arg Arg Leu Val Ser Glu Lys Val Gly Gln Ala Cys
                85                  90                  95

Cys Arg Pro Ile Ala Phe Asp Asp Asp Leu Ser Phe Leu Asp Asp Asn
            100                 105                 110

Leu Val Tyr His Ile Leu Arg Lys His Ser Ala Lys Arg Cys Gly Cys
        115                 120                 125

Ile

<210> SEQ ID NO 36
<211> LENGTH: 387
<212> TYPE: DNA
<213> ORGANISM: Artificial Sequence
<220> FEATURE:
<223> OTHER INFORMATION: Synthetic Construct

<400> SEQUENCE: 36
atggctaccg gcagcaggac ctctctgctg ctggccttcg gcctgctgtg cctgccctgg      60
ctgcaggaag cagcgccag gggtcaacgg ggcaagcaga ggggctgcgt gctgaccgcc     120
atccacctga acgtgaccga cctgggcctg ggctacgaga ccaaggagga gctgatcttc     180
aggtactgca gcggcagctg cgacgccgcc gagaccacct acgacaagat cctggccaac     240
ctgagcaaga caagcggct ggtctccgag aaggtgggcc aggcctgctg caggcccatc     300
gccttcgacg acgacctgag cttcctggac gacaacctgg tgtaccacat cctgaggaag     360
cacagcgcca gagatgcgg ctgcatc                                          387

<210> SEQ ID NO 37
<211> LENGTH: 129
<212> TYPE: PRT
<213> ORGANISM: Artificial Sequence
<220> FEATURE:
<223> OTHER INFORMATION: Synthetic Construct

<400> SEQUENCE: 37

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Arg Gly Gln Arg Gly Lys
            20                  25                  30

Gln Arg Gly Cys Val Leu Thr Ala Ile His Leu Asn Val Thr Asp Leu
        35                  40                  45

Gly Leu Gly Tyr Glu Thr Lys Glu Glu Leu Ile Phe Arg Tyr Cys Ser
```

```
                 50                  55                  60
Gly Ser Cys Asp Ala Ala Glu Thr Thr Tyr Asp Lys Ile Leu Ala Asn
 65                  70                  75                  80

Leu Ser Lys Asn Lys Arg Leu Val Ser Glu Lys Val Gly Gln Ala Cys
                 85                  90                  95

Cys Arg Pro Ile Ala Phe Asp Asp Leu Ser Phe Leu Asp Asp Asn
                100                 105                 110

Leu Val Tyr His Ile Leu Arg Lys His Ser Ala Lys Cys Gly Cys
                115                 120                 125

Ile

<210> SEQ ID NO 38
<211> LENGTH: 129
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (79)..(79)
<223> OTHER INFORMATION: Xaa at position 79 is Lys or Ala
<220> FEATURE:
<221> NAME/KEY: MISC_FEATURE
<222> LOCATION: (83)..(83)
<223> OTHER INFORMATION: Xaa at position 83 is Arg or Lys
<220> FEATURE:
<221> NAME/KEY: MISC_FEATURE
<222> LOCATION: (85)..(85)
<223> OTHER INFORMATION: Xaa at position 85 is Arg or Lys
<220> FEATURE:
<221> NAME/KEY: MISC_FEATURE
<222> LOCATION: (120)..(120)
<223> OTHER INFORMATION: Xaa at position 120 is Lys or Glu
<220> FEATURE:
<221> NAME/KEY: MISC_FEATURE
<222> LOCATION: (125)..(125)
<223> OTHER INFORMATION: Xaa at position 125 is Arg or Glu

<400> SEQUENCE: 38

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Arg Gly Gln Arg Gly Lys
                 20                  25                  30

Gln Arg Gly Cys Val Leu Thr Ala Ile His Leu Asn Val Thr Asp Leu
                 35                  40                  45

Gly Leu Gly Tyr Glu Thr Lys Glu Glu Leu Ile Phe Arg Tyr Cys Ser
             50                  55                  60

Gly Ser Cys Asp Ala Ala Glu Thr Thr Tyr Asp Lys Ile Leu Xaa Asn
 65                  70                  75                  80

Leu Ser Xaa Asn Xaa Arg Leu Val Ser Glu Lys Val Gly Gln Ala Cys
                 85                  90                  95

Cys Arg Pro Ile Ala Phe Asp Asp Leu Ser Phe Leu Asp Asp Asn
                100                 105                 110

Leu Val Tyr His Ile Leu Arg Xaa His Ser Ala Lys Xaa Cys Gly Cys
                115                 120                 125

Ile

<210> SEQ ID NO 39
<211> LENGTH: 46
<212> TYPE: DNA
<213> ORGANISM: Artificial Sequence
<220> FEATURE:
<223> OTHER INFORMATION: Synthetic Construct
```

<400> SEQUENCE: 39
tatacatatg cgtggacaac gtggtaaaca acgtggttgt gtgctg     46

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct

<400> SEQUENCE: 40
ggtgctcgag ttattaaatg cagccgcaac gtttcgcgct     40

<210> SEQ ID NO 41
<211> LENGTH: 26
<212> TYPE: DNA
<213> ORGANISM: Artificial Sequence
<220> FEATURE:
<223> OTHER INFORMATION: Synthetic Construct

<400> SEQUENCE: 41
gtctggtgag cgagaaagtg ggtcag     26

<210> SEQ ID NO 42
<211> LENGTH: 26
<212> TYPE: DNA
<213> ORGANISM: Artificial Sequence
<220> FEATURE:
<223> OTHER INFORMATION: Synthetic Construct

<400> SEQUENCE: 42
ctgacccact ttctcgctca ccagac     26

<210> SEQ ID NO 43
<211> LENGTH: 57
<212> TYPE: DNA
<213> ORGANISM: Artificial Sequence
<220> FEATURE:
<223> OTHER INFORMATION: Synthetic Construct

<400> SEQUENCE: 43
cctatgataa aatcctggca aacctgagca agaacaaacg tctggtgagc gagaaag     57

<210> SEQ ID NO 44
<211> LENGTH: 57
<212> TYPE: DNA
<213> ORGANISM: Artificial Sequence
<220> FEATURE:
<223> OTHER INFORMATION: Synthetic Construct

<400> SEQUENCE: 44
ctttctcgct caccagacgt tgttcttgc tcaggtttgc caggatttta tcatagg     57